US011359005B2

(12) United States Patent
Cui et al.

(10) Patent No.: US 11,359,005 B2
(45) Date of Patent: Jun. 14, 2022

(54) SUPRAMOLECULAR HIGH AFFINITY PROTEIN-BINDING SYSTEM FOR PURIFICATION OF BIOMACROMOLECULES

(71) Applicants: THE JOHNS HOPKINS UNIVERSITY, Baltimore, MD (US); BRISTOL-MYERS SQUIBB COMPANY, Princeton, NJ (US)

(72) Inventors: Honggang Cui, Lutherville, MD (US); Yi Li, Baltimore, MD (US); Xuankuo Xu, Boxborough, MA (US); Lye Lin Lock, Maynard, MA (US); Zhengjian Li, Sudbury, MA (US)

(73) Assignees: THE JOHNS HOPKINS UNIVERSITY, Baltimore, MD (US); BRISTOL-MYERS SQUIBB COMPANY, Princeton, NJ (US)

( * ) Notice: Subject to any disclaimer, the term of this patent is extended or adjusted under 35 U.S.C. 154(b) by 141 days.

(21) Appl. No.: 16/498,675

(22) PCT Filed: Mar. 28, 2018

(86) PCT No.: PCT/US2018/024721
§ 371 (c)(1),
(2) Date: Sep. 27, 2019

(87) PCT Pub. No.: WO2018/183417
PCT Pub. Date: Oct. 4, 2018

(65) Prior Publication Data
US 2020/0062827 A1 Feb. 27, 2020

Related U.S. Application Data

(60) Provisional application No. 62/478,886, filed on Mar. 30, 2017.

(51) Int. Cl.
| C07K 16/06 | (2006.01) |
| B01D 15/38 | (2006.01) |
| B01J 20/24 | (2006.01) |
| B01J 20/28 | (2006.01) |
| C07K 14/31 | (2006.01) |

(52) U.S. Cl.
CPC ........ C07K 16/065 (2013.01); B01D 15/3809 (2013.01); B01J 20/24 (2013.01); B01J 20/28023 (2013.01); C07K 14/31 (2013.01)

(58) Field of Classification Search
CPC . B01D 15/3809; B01J 20/24; B01J 20/28023; C07K 14/31; C07K 16/00; C07K 16/065; C07K 1/303
See application file for complete search history.

(56) References Cited

U.S. PATENT DOCUMENTS

| 5,223,409 A | 6/1993 | Ladner et al. |
| 5,403,484 A | 4/1995 | Ladner et al. |
| 5,427,908 A | 6/1995 | Dower et al. |
| 5,476,996 A | 12/1995 | Wilson et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,698,767 A | 12/1997 | Wilson et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |

(Continued)

FOREIGN PATENT DOCUMENTS

| WO | 199203918 A1 | 3/1992 |
| WO | 199312227 A1 | 6/1993 |

(Continued)

OTHER PUBLICATIONS

Yi Li, Yuzhu Wang, Shih-Hao Ou, Lye Lin Lock, Xuankuo Xu, Sanchayita Ghose, Zheng Jian Li, and Honggang Cui, "Conformation Preservation of α-Helical Peptides within Supramolecular Filamentous Assemblies," Biomacromolecules, 2017, vol. 18, No. 11, pp. 3611-3620; Publication Date: Sep. 11, 2017.*

(Continued)

*Primary Examiner* — Galina M. Yakovleva
(74) *Attorney, Agent, or Firm* — Casimir Jones, S.C.; Thomas A. Isenbarger

(57) ABSTRACT

In certain embodiments, the present invention provides novel antibody purification methods and systems using a potentially simple and cost-efficient means. In some embodiments, customized Z-33 derived from *Staphylococcus aureus* Protein A is used to construct immuno-amphiphile molecules which can assemble into immunofibers in aqueous solution with bioactive epitopes on the surface and have IgG binding ability.

9 Claims, 10 Drawing Sheets
Specification includes a Sequence Listing.

(56) References Cited

U.S. PATENT DOCUMENTS

| | | | |
|---|---|---|---|
| 6,172,197 B1 | 1/2001 | McCafferty et al. | |
| 6,197,927 B1 | 3/2001 | Braisted et al. | |
| 6,521,404 B1 | 2/2003 | Griffiths et al. | |
| 6,544,731 B1 | 4/2003 | Griffiths et al. | |
| 6,555,313 B1 | 4/2003 | Griffiths et al. | |
| 6,582,915 B1 | 6/2003 | Griffiths et al. | |
| 6,593,081 B1 | 7/2003 | Griffiths et al. | |
| 2020/0197902 A1* | 6/2020 | Cui | B01J 20/3475 |

FOREIGN PATENT DOCUMENTS

| | | |
|---|---|---|
| WO | 199425585 A1 | 11/1994 |
| WO | 199713852 A1 | 4/1997 |
| WO | 199824884 A1 | 6/1998 |
| WO | 199945962 A1 | 9/1999 |
| WO | 200114424 A1 | 3/2001 |
| WO | 200243478 A2 | 6/2002 |
| WO | WO 2019/036631 A1 | 2/2019 |

OTHER PUBLICATIONS

Deng et al., "Self-assembly of Peptide—Amphiphile C12—Aβ(11-17) into Nanofibrils," J. Phys. Chem. B, 2009, vol. 113, No. 25, pp. 8539-8531.*

Forns et al., "Induction of protein-like molecular architecture by monoalkyl hydrocarbon chains," Biopolymers, 2000, vol. 54, issue 7, pp. 531-546.*

Missirlis et al., "Mechanisms of peptide amphiphile internalization by SJSA-1 cells in vitro," Biochemistry, 2009, vol. 48, No. 15, pp. 3304-3314.*

Li et al., "Bioinspired supramolecular engineering of self-assembling immunofibers for high affinity binding of immunoglobulin G," Biomaterials, vol. 178, Sep. 2018, pp. 448-457; available online Apr. 16, 2018.*

A printout retrieved from https://www.immunoglobe.com/epitope-selection.html on Sep. 23, 2021.*

Morrison et al., Chimeric human antibody molecules: mouse antigen-binding domains with human constant region domains Proc. Natl. Acad. Sci. USA 81:6851-6855 (1984).

Jones et al., Replacing the complementarity-determining regions in a human antibody with those from a mouse Nature 321:522-525 (1986).

Riechmann et al., Reshaping human antibodies for therapy Nature 332:323-329 (1988).

Presta, Antibody engineering., Curr. Op. Struct. Biol. 2:593-596 (1992).

Taylor et al. A transgenic mouse that expresses a diversity of human sequence heavy and light chain immunoglobulins (1992) Nucleic Acids Research 20:6287-6295.

Chen et al. Immunoglobulin gene rearrangement in B cell deficient mice generated by targeted deletion of the JH locus (1993) International Immunology 5: 647-656.

Palmer et al., Molecular self-assembly into one-dimensional nanostructures. Accounts of chemical research 2008, 41 (12), 1674-1684.

Tuaillon et al. Human immunoglobulin heavy-chain minilocus recombination in transgenic mice: gene-segment use in mu and gamma transcripts.(1993) Proc. Natl. Acad. Sci. USA 90:3720-3724.

Choi et al., Transgenic mice containing a human heavy chain immunoglobulin gene fragment cloned in a yeast artificial chromosome (1993) Nature Genetics 4:117-123.

Chen et al., B cell development in mice that lack one or both immunoglobulin kappa light chain genes. (1993) EMBO J. 12: 821-830.

Tuaillon et al., Biased utilization of DHQ52 and JH4 gene segments in a human Ig transgenic minilocus is independent of antigenic selection. (1994) J. Immunol. 152:2912-2920.

Taylor et al., Human immunoglobulin transgenes undergo rearrangement, somatic mutation and class switching in mice that lack endogenous IgM. (1994) International Immunology 6: 579-591.

Fishwild et al. High-avidity human IgG kappa monoclonal antibodies from a novel strain of minilocus transgenic mice. (1996) Nature Biotechnology 14: 845-851.

Jaenicke, A rapid micromethod for the determination of nitrogen and phosphate in biological material., Anal. Biochem., 61.2 (1974): 623-627.

Strable, E., et al., "Unnatural Amino Acid Incorporation into Virus-Like Particles" Bioconjug Chem. Apr. 2008 ; 19(4): 866-875. doi:10.1021/bc700390r.

Kenan, D., et al., "Peptide-PEG Amphiphiles as Cytophobic Coatings for Mammalian and Bacterial Cells" Chemistry & Biology 13, 695-700, Jul. 2006 DOI 10.1016/j.chembiol.2006.06.013.

Pille, J., et al., "General Strategy for Ordered Noncovalent Protein Assembly on Well-Defined Nanoscaffolds" Biomacromolecules 2013, 14, 4351-4359; dx.doi.org/10.1021/bm401291u.

Sorokina, I.A., et al., "Guidance manual, large laboratory practical course 2" Biochemistry of Proteins and Peptides, Rostov-on-Don, 2010, p. 96.

Altunbas et al., Encapsulation of curcumin in self-assembling peptide hydrogels as injectable drug delivery vehicles. Biomaterials 2011, 32 (25), 5906-14.

Chow et al., Self-assembling nanostructures to deliver angiogenic factors to pancreatic islets. Biomaterials 2010, (24), 6154-61.

Koutsopoulos et al., Two-layered injectable self-assembling peptide scaffold hydrogels for long-term sustained release of human antibodies. J Control Release 2012, 160 (3), 451-8.

Lock et al., Tuning Cellular Uptake of Molecular Probes by Rational Design of Their Assembly into Supramolecular Nanoprobes. Journal of the American Chemical Society 2016, 138 (10), 3533-3540.

Cheetham et al., Supramolecular Nanostructures Formed by Anticancer Drug Assembly. Journal of the American Chemical Society 2013, 135 (8), 2907-2910.

Hu et al., Spatiotemporal control of the creation and immolation of peptide assemblies. Coordination Chemistry Reviews 2016, 320, 2-17.

Ma et al., Building nanostructures with drugs. Nano Today 2016, 11 (1), 13-30.

Black et al., Self-Assembled Peptide Amphiphile Micelles Containing a Cytotoxic T-Cell Epitope Promote a Protective Immune Response In Vivo. Adv Mater 2012, 24 (28), 3845-3849.

Shimada et al., Wormlike micelle formation in peptide-lipid conjugates driven by secondary structure transformation of the headgroups. The journal of physical chemistry. B 2009, 113 (42), 13711-4.

Trent et a., Structural properties of soluble peptide amphiphile micelles. Soft Matter 2011, 7 (20), 9572-9582.

Cui et al., self-ssembly of peptide amphiphiles: from molecules to nanostructures to biomaterials. Biopolymers 2010, 94(1), 1-18.

Hartgerink et al., Self-assembly and mineralization of peptideamphiphile nanofibers. Science 2001, 294 (5547), 1684-1688.

Niece et al., Self-assembly combining two bioactive peptide-amphiphile molecules into nanofibers by electrostatic attraction. Journal of the American Chemical Society 2003, 125 (24), 7146-7147.

Webber et al., Development of bioactive peptide amphiphiles for therapeutic cell delivery. Acta Biomater 2010, 6 (1), 3-11.

Cui et al., Amino Acid Sequence in Constitutionally Isomeric Tetrapeptide Amphiphiles Dictates Architecture of One-Dimensional Nanostructures. Journal of the American Chemical Society 2014, 136 (35), 12461-12468.

Moyer et al., pH and Amphiphilic Structure Direct Supramolecular Behavior in Biofunctional Assemblies. Journal of the American Chemical Society 2014, 136 (42), 14746-14752.

Webber et al., Reprint of: Development of bioactive peptide amphiphiles for therapeutic cell delivery. Acta biomaterialia 2015, 23, S42-S51.

Paramonov et al., Self-assembly of peptide-amphiphile nanofibers: the roles of hydrogen bonding and amphiphilic backing. Journal of the American Chemical Society 2006, 128 (22), 7291-7298.

Arslan et al., Bioactive supramolecular peptide nanofibers for regenerative medicine. Advanced healthcare materials 2014, 3 (9), 1357-1376.

(56) References Cited

OTHER PUBLICATIONS

Kokkoli et al., Selfassembly and applications of biomimetic and bioactive peptide-amphiphiles. Soft Matter 2006, 2 (12), 1015.
Rudra et al., Modulating adaptive immune responses to peptide self-assemblies. Acs Nano 2012, 6(2), 1557-1564.
Ecker et al., The therapeutic monoclonal antibody market. MAbs 2015, 7 (1), 9-14.
Low et al., Future of antibody purification. J Chromatogr B Analyt Technol Biomed Life Sci 2007, 848 (1), 48-63.
Shukla et al., Downstream processing of monoclonal antibodies—application of platform approaches. J Chromatogr B Analyt Technol Biomed Life Sci 2007, 848 (1), 28-39.
Deisenhofer., Crystallographic refinement and atomic models of a human Fc fragment and its complex with fragment B of protein A from *Staphylococcus aureus* at 2.9- and 2.8-. ANG resolution. Biochemistry 1981, 20 (9), 2361-2370.
Moks et al., Staphylococcal protein A consists of five IgG-binding domains. European Journal of Biochemistry 1986, 156 (3), 637-643.
Braisted et al., Minimizing a binding domain from protein A. Proceedings of the National Academy of Sciences 1996, 93 (12), 5688-5692.
Nilsson et al., A synthetic IgG-binding domain based on staphylococcal protein A. Protein engineering 1987, 1 (2), 107-113.
Starovasnik et al., Structural mimicry of a native protein by a minimized binding domain. Proceedings of the National Academy of Sciences 1997, 94 (19), 10080-10085.
Olszewski et al.,Folding simulations and computer redesign of protein A three-helix bundle motifs. Proteins 1996, 25.
Boutelje et al., Human immunodeficiency viral protease is catalytically active as a fusion protein: characterization of the fusion and native enzymes produced in *Escherichia coli*. Archives of biochemistry and biophysics 1990, 283 (1), 141-149.
Hober et al., Protein A chromatography for antibody purification. J Chromatogr B Analyt Technol Biomed Life Sci 2007, 848 (1), 40-7.
Cuatrecasas., Protein purification by affinity chromatography. J. Biol. Chem 1970, 245 (12), 3050.
Huse et al., Purification of antibodies by affinity chromatography. Journal of biochemical and biophysical methods 2002, 51 (3), 217-231.
Hassouneh et al., Elastin-like polypeptides as a purification tag for recombinant proteins. Curr Protoc Protein Sci 2010, Chapter 6, Unit 6 11.
Sheth et al., Affinity precipitation of a monoclonal antibody from an industrial harvest feedstock using an ELP-Z stimuli responsive biopolymer. Biotechnol Bioeng 2014, 111 (8), 1595-603.
Handlogten et al., Nonchromatographic affinity precipitation method for the purification of bivalently active pharmaceutical antibodies from biological fluids. Analytical chemistry 2013, 85 (10), 5271-5278.
Eisen et al., Variations in Affinities of Antibodies during the Immune Response*. Biochemistry 1964, 3 (7), 996-1008.
Madan et al., ELP-z and ELP-zz capturing scaffolds for the purification of immunoglobulins by affinity precipitation. J Biotechnol 2013, 163 (1), 10-6.
Sheth et al., Development of an ELP-Z based mAb affinity precipitation process using scaled-down filtration techniques. J Biotechnol 2014, 192 Pt A, 11-9.
Kawashima et al., EpCAM- and EGFR-targeted selective gene therapy for biliary cancers using Z33-fiber modified adenovirus. Int J Cancer 2011, 129 (5), 1244-53.
Kickhoefer et al., Targeting vault nanoparticles to specific cell surface receptors. Acs Nano 2008, 3 (1), 27-36.
Freire et al., Characterisation of ligand binding by calorimetry. In Biophysical Approaches Determining Ligand Binding to Biomolecular Targets, 2011; pp. 275-299.
Wiseman et al., Rapid measurement of binding constants and heats of binding using a new titration calorimeter. Analytical biochemistry 1989, 179 (1), 131-137.
Demers et al., Binding mechanism of an SH3 domain studied by NMR and ITC. Journal of the American Chemical Society 2009, 131 (12), 4355-4367.
Van Eldijk et al., Thermodynamic investigation of Z33-antibody interaction leads to selective purification of human antibodies. J Biotechnol 2014, 179, 32-41.
Lund et al., Exploring variation in binding of Protein A and Protein G to immunoglobulin type G by isothermal titration calorimetry. J Mol Recognit 2011, 24 (6), 945-52.
Kohler et al., Continuous cultures of fused cells secreting antibody of predefined specificity., Nature 256:495 (1975).
Clackson et al., Making antibody fragments using phage display libraries., Nature 352:624-628 (1991).
Marks et al., By-passing immunization: human antibodies from V-gene libraries displayed on phage J. Mol. Biol. 222:581-597 (1991).
Extended European Search Report dated Nov. 18, 2020, European Application No. 18775537.6, 8 pages.

* cited by examiner

FIGURES 3A-3D
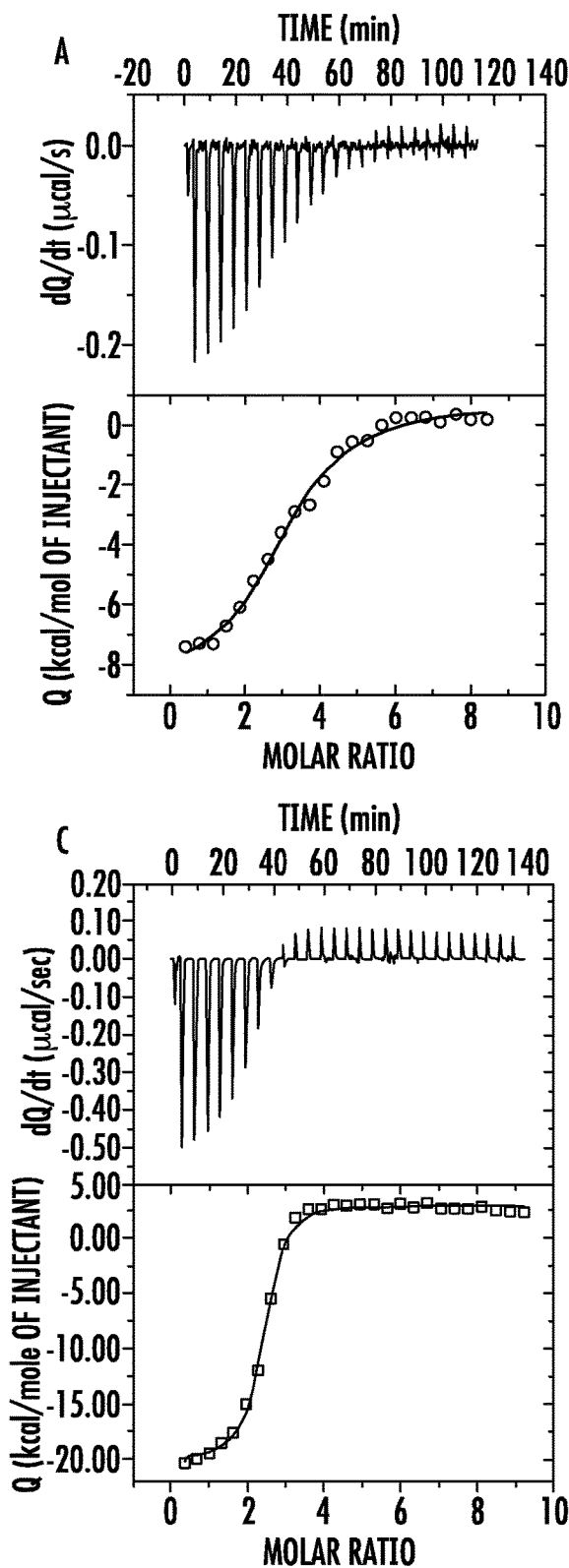
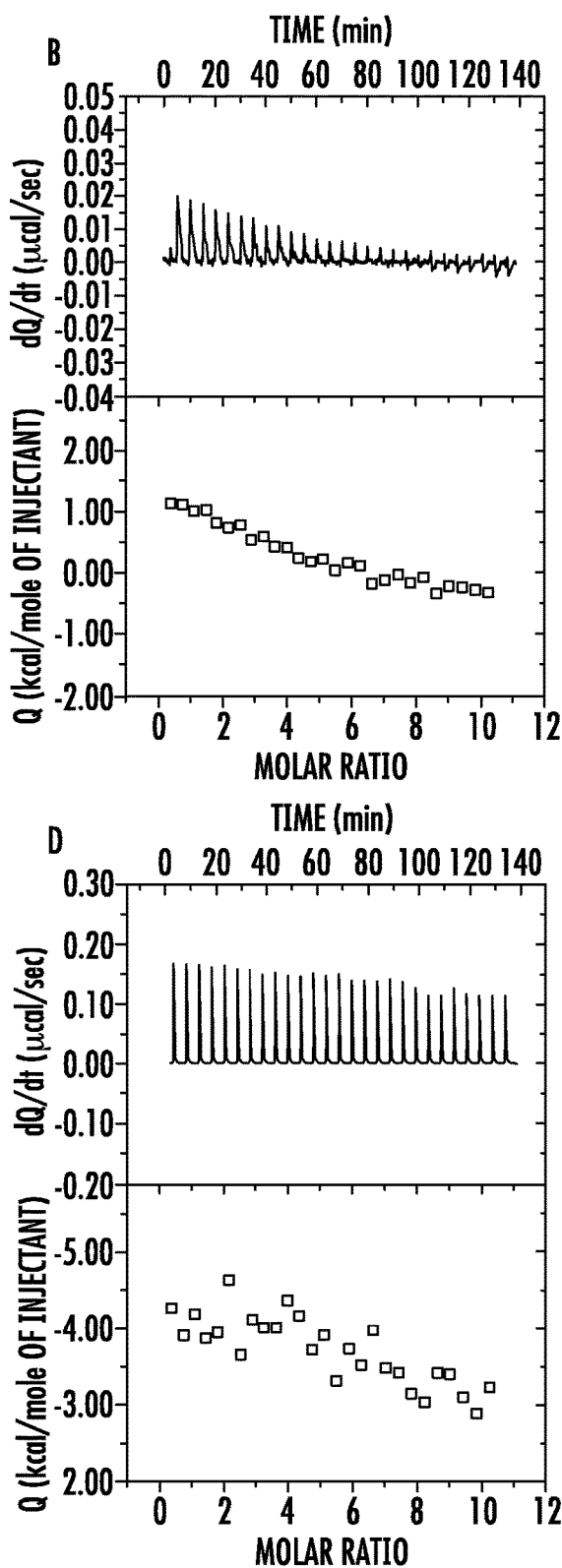

US 11,359,005 B2

SUPRAMOLECULAR HIGH AFFINITY PROTEIN-BINDING SYSTEM FOR PURIFICATION OF BIOMACROMOLECULES

REFERENCE TO RELATED APPLICATIONS

This application is a 35 U.S.C. § 371 U.S. national entry of International Application PCT/US2018/024721, having an international filing date of Mar. 28, 2018, which claims the benefit of U.S. Provisional Application No. 62/478,886, filed Mar. 30, 2017, the content of each of the aforementioned applications is herein incorporated by reference in their entirety.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Mar. 20, 2018, is named P14162-02_ST25.txt and is 1,016 bytes in size.

BACKGROUND OF THE INVENTION

Supramolecular one-dimensional (1D) nanostructures formed by self-assembly of synthetic or naturally occurring peptides and their derivatives have received rapidly increasing interest over the past three decades due to their important applications in regenerative medicine, drug delivery and disease diagnostics.[1-10] For example, the Stupp laboratory has designed and synthesized a series of peptide amphiphiles (PAs) by conjugating linear hydrocarbons onto a β-sheet-forming sequence that could self-assemble into supramolecular nanofibers under the physiological conditions.[2, 11-16] To impart the PA assemblies with the desired bioactivities to interface with biology, a variety of bioactive epitopes, such as cell adhesion motif RGD and neurite-promoting sequence IKVAV (SEQ ID NO: 2), have been incorporated into the molecular design.[13, 17-20] In one example, Webber et al. investigated bioactive PA nanofibers displaying the RGDS (SEQ ID NO: 3) epitope on the surface therapeutic delivery of bone-marrow mononuclear cells (BMNCs), implying an enhanced biological adhesion.[14] This direct placemen of bioactive peptide on either C- or N-terminus of a self-assembling peptide motif has become a popular strategy to create bioactive materials for a specific biomedical application. In an effort to modulate immunogenicity of peptide assemblies, Collier and coworkers covalently linked the self-assembling peptide Q11 to an antigen OVA peptide and found that the resultant supramolecular OVA-Q11 nanofibers possess enhanced immunogenicity.[21]

High affinity antibody-binding particles and materials are receiving rapidly growing interest in the pharmaceutical industry, driven by the increasing demand of monoclonal antibodies for biological therapeutics.[22-24] Protein A, a well-known antibody-binding ligand, has the capacity of specific binding to the Fc-portion of IgG from most mammalian species, including human.[25-26] However, the large size of protein A limits its industrial application, and as such a number of synthetic and minimized domains of protein A have been designed and studied.[27-29] The Z-domain of protein A is the first and most famous synthetic domain with 59 amino acid residues and a $K_d$ of ~10 nM when binding to IgG1.[30-31] To further minimize the Z-domain of protein A, a two-helix derivative Z33 was designed without significantly changing the binding affinity ($K_d$=43 nM).[27] While a high affinity ligand has been identified, the way to present ligands on a desired substrate is equally essential for the antibody purification process. In pharmaceutical industry, antibody purification mainly relies on affinity chromatography based on immobilization of antibody binding ligands (e.g., protein A) with high selectivity but suffering from the high chromatography media cost and limited capture productivity.[32-34] It is only until recently that affinity precipitation became an attractive alternative to traditional chromatographic methods by offering effective purification and potentially debottlenecking batch throughput using a relatively simple process.[35-38]

A typical example of affinity precipitation is the use of elastin-like-protein (ELP) fused Z-domain to precipitate IgG through the temperature and salt triggered solubility transition of ELP.[39-40] However, the high mass of ELP expressed by bacteria, limited binding sites on each ELP fused ligand, and potential denaturation of antibody at elevated temperature promote the interest of finding the new substrates to present antibody-binding ligands.

Inspired by the elegant molecular design of self-assembling peptide amphiphiles, we investigated the way of incorporating the protein A mimicking peptide Z33 into self-assembling immuno-amphiphiles (IAs) and explored its binding ability to the target antibody in the self-assembled state. The binding affinity between the self-assembled immunofibers (IFs) and therapeutic IgG were investigated using isothermal titration calorimetry (ITC), suggesting that the Z33 containing IFs maintains its high IgG binding affinity.

SUMMARY OF THE INVENTION

Many one-dimensional (1D) nanostructures are constructed by self-assembly of peptides or peptide conjugates containing a short β-sheet sequence as the core building motif essential for the intermolecular hydrogen bonding that promotes directional, anisotropic growth of the resultant assemblies. While this molecular design strategy has led to the successful production of a plethora of bioactive filamentous β-sheet assemblies for interfacing with cells, concerns associated with potential toxicity reminiscent of amyloid fibrils have promoted other supramolecular crafting strategies with α-helical peptides.

Thus far, there have been numerous studies in the literature that have demonstrated that biologically active peptides can be successfully incorporated into supramolecular peptide nanostructures while maintaining their bioactivities. However, in the cases where the epitope has to retain an α-helical conformation to be bioactive, there seems to be a spacing incompatibility issue between the use of β-sheet-forming sequence and the presentation of α-helical motif. In this context, the inventors now show the direct conjugation of the protein A mimicking peptide Z33, a motif containing two α-helices, to linear hydrocarbons, to create two self-assembling immuno-amphiphiles with high binding affinity to monoclonal antibodies, and demonstrate for the first time that these inventive supramolecular immunofibers (IFs) can be utilized for precipitation and purification of monoclonal antibody immunoglobulin G (IgG).

In accordance with some embodiments, the present invention comprises the direct conjugation of the Protein A of *Staphylococcus aureus* mimicking peptide Z33, having the amino acid sequence FNMQQQRRFYEALHDPNLNE-EQRNAKIKSIRDD (SEQ ID NO: 1), a motif containing two α-helices, to linear hydrocarbons to create self-assembling immuno-amphiphiles. The results show that the resulting amphiphilic peptides can, despite lacking the essential β-sheet segment, effectively associate under physiological conditions, into supramolecular immunofibers (IFs) while preserving their native α-helical conformation. Isothermal titration calorimetry measurements confirmed that these self-assembling immunofibers can bind to the immunoglobulin G (IgG) antibody with high specificity at pH 7.4, but no detectable binding occurred in elution buffer, pH 2.8.

In accordance with some further embodiments, it was demonstrated that the IFs of the present invention have pH dependent specific binding which enables the precipitation and purification of the target IgG antibodies.

Thus, in some embodiments, the supramolecular engineering of protein binding peptides into filamentous assemblies are useful for effective protein purification.

In accordance with an embodiment, the present invention provides an immuno-amphiphile comprising an antibody binding peptide conjugated to a linear hydrocarbon chain.

In accordance with an embodiment, the present invention provides an immuno-amphiphile comprising an antibody binding peptide conjugated to a linear hydrocarbon chain and wherein the peptide takes an α-helical conformation when in an aqueous solution at physiological pH.

In accordance with an embodiment, the present invention provides an immuno-amphiphile comprising an antibody binding peptide conjugated to a linear hydrocarbon chain, wherein the antibody binding peptide has a hydrophilic amino acid sequence of the Z33 peptide of Protein A of *Staphylococcus aureus*, or a functional portion or fragment or derivative thereof.

In accordance with another embodiment, the present invention provides an immuno-amphiphile comprising an antibody binding peptide conjugated to a linear hydrocarbon chain, wherein the antibody binding peptide has the amino acid sequence FNMQQQRRFYEALHDPNLNEEQRNAKIKSIRDD (SEQ ID NO: 1), or a functional portion or fragment or derivative thereof.

In accordance with another embodiment, the present invention provides a method for purification of an antibody or an Fc fusion protein, comprising the steps of: a) dissolving the immuno-amphiphile in an aqueous solution at physiological pH and aging overnight to make it self-assemble into immuofibers (IFs); b) mixing a sample containing the antibody or Fc fusion protein with the IFs, and allowing the IFs to bind the Fc portion of the antibody or Fc fusion protein and form an immunofiber-antibody complex or an immunofiber-Fc fusion protein complex in solution; c) separating the immunofiber-antibody complex or immunofiber-Fc fusion protein complex from the solution by adding salt and centrifugation; and d) dissociating the IFs from the antibody or Fc fusion protein and collecting the unbound antibody or Fc fusion protein. For example, the IFs may be separated from the antibody or Fc fusion protein by lowering the pH to elution condition and filtration or microfiltration.

BRIEF DESCRIPTION OF THE DRAWINGS

FIGS. 3A-3D. ITC profiles for the titration of 100 μM C12-Z33 into a solution of 2 μM IgG1 at 15° C. in (A) PBS buffer, pH 7.4, and (B) IgG elution buffer, pH 2.8. ITC profiles for the titration of 100 μM (C) Z33 and (D) C12-SZ33 into 2 μM IgG1 in PBS at 15° C., pH 7.4.

DETAILED DESCRIPTION OF THE INVENTION

Figures 1A, 1B, 1C:
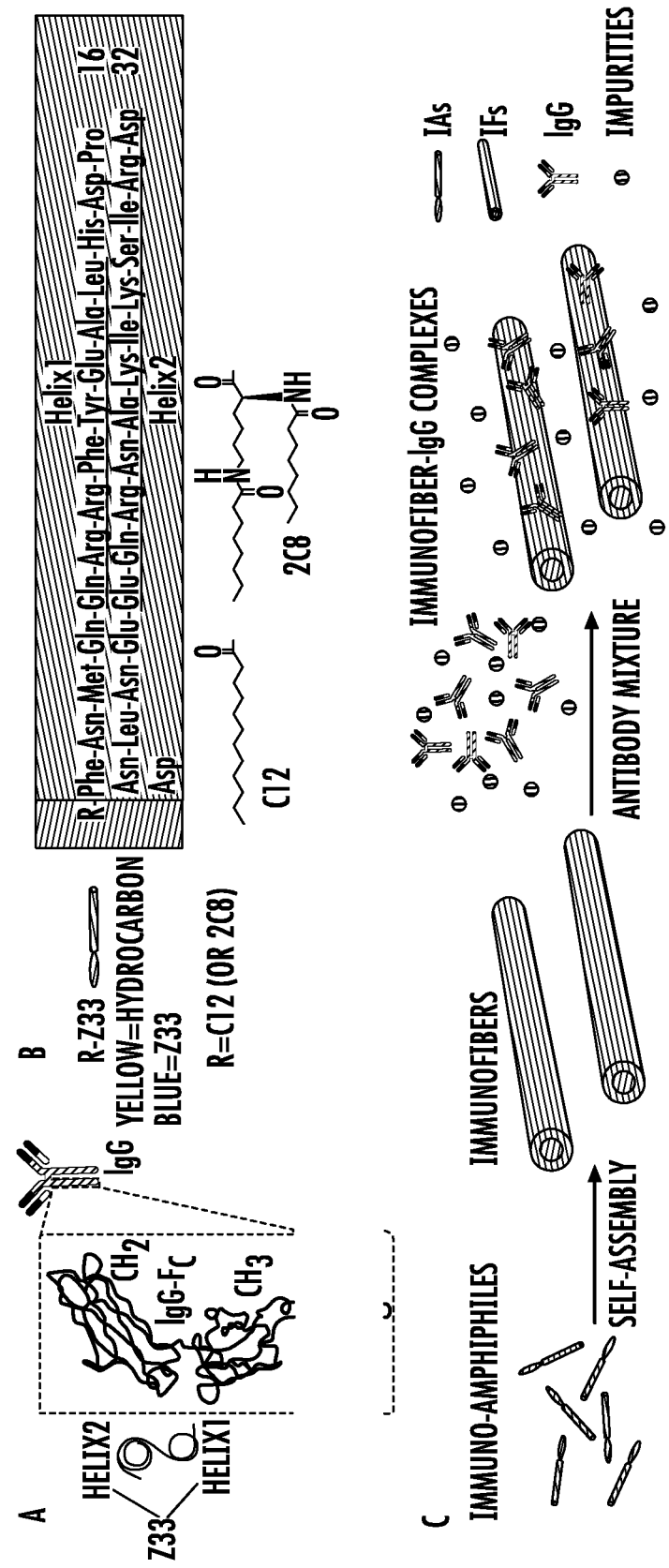
FIGS. 1A-1C. (1A) Schematic illustration of the Z33 peptide binding to Fc-portion of IgG. (1B) The sequences of C12-Z33 and 2C8-Z33. Alkyl groups and Z33 are indicated with the yellow and blue shaded areas, respectively. The two α-helices in Z33 peptide are underlined. (1C) Schematic illustration of the self-assembly of R-Z33 IFs and the binding between IFs and IgG.

Staphylococcal protein A (SPA) is a protein originally found in the cell wall of *Staphylococcus aureus*. It is composed of five homologous domains that fold into a three-helix bundle. Protein A plays an important role in immunology due to its specific binding to the Fc-portion of immunoglobulin G (aka IgG) from most mammalian species, including human. Extensive structural and biochemical studies of protein A have been conducted. The first gene encoding SPA was cloned, sequenced and expressed in 1984 followed by numerous synthetic and minimized IgG-binding domain based on protein A. Among them Z-58 domain is the first and most famous synthetic domain to be widely used in affinity chromatography and affinity precipitation. Another minimized binding domain Z-33 was obtained in 1996 without significantly changing the function of the molecule.

In accordance with several embodiments, the present invention provides methods for the modification and/derivatization of the amino acid sequence of the antibody binding domain of SPA into immuno-amphiphiles which serve as the building unit for IFs. Described herein are examples of the design and creation of IFs useful in binding IgG antibodies or portions or fragments thereof. Once immunofibers are formed in aqueous solution at physiological pH ranges, the exposed bioactive epitopes (binding sites) displayed on the surface are able to specifically bind IgG.

In accordance with an embodiment, the present invention provides an immuno-amphiphile comprising an antibody binding peptide conjugated to a linear hydrocarbon chain.

In accordance with an embodiment, the present invention provides an immuno-amphiphile comprising an antibody binding peptide conjugated to a linear hydrocarbon chain and wherein the immuno-amphiphile has an α-helical conformation when in an aqueous solution at physiological pH.

In accordance with an embodiment, the present invention provides an immuno-amphiphile comprising an antibody binding peptide conjugated to a linear hydrocarbon chain, wherein the antibody binding peptide has a hydrophilic amino acid sequence of the Z33 peptide of Protein A of *Staphylococcus aureus*, or a functional portion or fragment or derivative thereof.

In accordance with another embodiment, the present invention provides an immuno-amphiphile comprising an antibody binding peptide conjugated to a linear hydrocarbon chain, wherein the antibody binding peptide has the amino acid sequence FNMQQQRRFYEALHDPNLNEEQRNAKIKSIRDD (SEQ ID NO: 1), or a functional portion or fragment or derivative thereof.

As used herein, the term "immuno-amphiphiles" means a molecule that can spontaneously associate into discrete, stable supramolecular nanostructures termed "immunofibers". Generally, the IFs can assemble in a pH range between about 2.8 to about 7.5. However, the binding properties are also pH dependent. Those IFs which are more positively charged are easier to associate with higher pH solutions, and conversely, negatively charged IFs will associate easier in lower pH solutions.

In some embodiments, a hydrophilic peptide is conjugated to a hydrocarbon tail having between 8 and 22 carbons, and is linear or can be branched. There is an upper limit to the number of carbons in view of solubility in an aqueous solution. The hydrophilic peptide increases the aqueous solubility of the nanostructure and can promote the formation of well-defined nanostructure architectures including, but not limited to, cylindrical or spherical micelles, hollow nanotubes, toroids, discs and vesicles, through preferred secondary structure formation, e.g. beta sheet, alpha helix, poly proline type-II helix, beta turn.

As used herein, the term "antibody binding peptide" means a peptide that has the ability to bind an antibody, or a specific portion of an antibody molecule, for example, the Fc portion, with high specificity, such as having a $K_d$ of between about $10^{-6}$ M to about $10^{-10}$ M.

In some embodiments, the antibody binding peptide is the hydrophilic amino acid sequence of the Z33 two-helix derivative peptide of the Z-domain of Protein A of *Staphylococcus aureus*, or a functional portion or fragment or derivative thereof.

As used herein, the Z33 peptide of Protein A has the amino acid sequence of FNMQQQRRFYEALHDPNLNEEQRNAKIKSIRDD (SEQ ID NO: 1).

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and non-natural amino acids. Many types of amino acid residues are useful in the polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

Reference herein to "derivatives" includes parts, fragments and portions of the inventive antibody binding peptides of the present invention. A derivative also includes a single or multiple amino acid substitution, deletion and/or addition. Homologues include functionally, structurally or sterochemically similar peptides. All such homologues are contemplated by the present invention.

Analogs and mimetics include molecules which include molecules which contain non-naturally occurring amino acids or which do not contain amino acids but nevertheless behave functionally the same as the peptide. Natural product screening is one useful strategy for identifying analogs and mimetics.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, omithine, sarcosine, 4-amino-3-hydroxy-6-methylheptanoic acid, 2-thienyl alanine and/or D-isomers of amino acids. A partial list of known non-natural amino acid contemplated herein is shown in Table 1.

TABLE 1

Non-natural Amino Acids

| Non-conventional amino acid | Code | Non-conventional amino acid | Code |
|---|---|---|---|
| α-aminobutyric acid | Abu | L-N-methylalanine | Nmala |
| α-amino-a-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine |  | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylasparatate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylorinithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |

TABLE 1-continued

Non-natural Amino Acids

| Non-conventional amino acid | Code | Non-conventional amino acid | Code |
|---|---|---|---|
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenylethylamino)cyclopropane | Nmbc | | |

Analogs of the subject peptides contemplated herein include modifications to side chains, incorporation of non-natural amino acids and/or their derivatives during peptide synthesis and the use of crosslinkers and other methods which impose conformational constraints on the peptide molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The term, "peptide," as used herein, includes a sequence of from four to 100 amino acid residues in length, preferably about 10 to 80 residues in length, more preferably, 15 to 65 residues in length, and in which the α-carboxyl group of one amino acid is joined by an amide bond to the main chain (α- or β-) amino group of the adjacent amino acid.

In accordance with some other embodiments, the immunofibers can be separated from bound antibodies using several filtration methods, such as, for example diafiltration.

In accordance with some embodiments, generally, the present invention provides methods for purification of an antibody or an Fc fusion protein by mixing the antibody or Fc fusion protein in a sample with the immunofibers of the present invention in an aqueous solution at physiological pH, and allowing the immunofibers to bind the Fc portion of the antibody or Fc fusion protein. In some embodiments, the immunofibers comprise the Z33 portion of Protein A and are specific for the Fc portion of antibodies. After a period of time to allow the immunofibers to bind, the immunofibers form immunofiber-antibody or immunofiber-Fc fusion protein complexes in solution. The complexes formed can then be separated from the unbound immunofibers and antibodies or Fc fusion proteins and other components in the sample by many known separation means, including, for example, salt-induced precipitation and centrifugation. The separated complexes can then be introduced into another solution at an acidic pH, where the immunofibers lose their binding affinity for the antibodies or Fc fusion proteins. The antibody or Fc fusion protein can then be separated from the dissociated immunofibers by filtration, such as diafiltration or other means, and the dissociated monomers can be removed as well.

As used herein, the term "sample" means any sample or solution or fluid or mixture containing an antibody of interest or an Fc fusion protein of interest which can be bound using the immunofibers of the present invention. In some embodiments, the sample can be a biological sample.

For example, the sample includes, for example, cell cultures, cell lysates, and clarified bulk (e.g., clarified cell culture supernatant). Optionally, the sample is produced from a host cell or organism that expresses the antibody or Fc fusion protein of interest (either naturally or recombinantly). For example, the cells in a cell culture include host cells transfected with an expression construct containing a nucleic acid that encodes an antibody or Fc fusion protein of interest. These host cells can be bacterial cells, fungal cells, insect cells or, preferably, animal cells grown in culture. Bacterial host cells include, but are not limited to E. coli cells. Examples of suitable E. coli strains include: HB101, DH5α, GM2929, JM109, KW251, NM538, NM539, and any E. coli strain that fails to cleave foreign DNA. Fungal host cells that can be used include, but are not limited to, Saccharomyces cerevisiae, Pichia pastoris and Aspergillus cells. Insect cells that can be used include, but are not limited to, Bombyx mori, Mamestra drassicae, Spodopterafrugiperda, Trichoplusia ni, Drosophilia melanogaster. A number of mammalian cell lines are suitable host cells, including for example, CHO, COS, PER.C6, TM4, VER0076, DXB11, MDCK, BRL-3A, W138, Hep G2, MMT, MRC 5, FS4, CHO, 293T, A431, 3T3, CV-1, C3H10T1/2, Colo205, 293, HeLa, L cells, BHK, HL-60, FRhL-2, U937, HaK, Jurkat cells, Rat2, BaF3, 32D, FDCP-1, PC12, Mlx, murine myelomas (e.g., SP2/0 and NS0) and C2C12 cells, as well as transformed primate cell lines, hybridomas, normal diploid cells, and cell strains derived from in vitro culture of primary tissue and primary explants.

In accordance with one or more embodiments of the present invention, it will be understood that the term "biological sample" or "biological fluid" includes, but is not limited to, any quantity of a substance from a living or formerly living patient or mammal or from cultured cells. Such substances include, but are not limited to, blood, serum, plasma, urine, cells, organs, tissues, bone, bone marrow, lymph, lymph nodes, synovial tissue, chondrocytes, synovial macrophages, endothelial cells, skin, cell cultures, cell lysates, and clarified bulk (e.g., clarified cell culture supernatant).

In certain specific embodiments of the invention, the protein purified using the present invention is an antibody. The term "antibody" is used in the broadest sense to cover monoclonal antibodies (including full length monoclonal antibodies), polyclonal antibodies, multispecific antibodies (e.g., bispecific antibodies), antibody fragments, immunoadhesins and antibody-immunoadhesin chimerias.

An "antibody fragment" includes at least the Fc portion of an antibody and typically an antigen binding or variable region thereof.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., Nature 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., Nature 352:624-628 (1991); Marks et al., J. Mol. Biol. 222:581-597 (1991); and U.S. Pat. Nos. 5,223,409; 5,403, 484; 5,571,698; 5,427,908 5,580,717; 5,969,108; 6,172,197; 5,885,793; 6,521,404; 6,544,731; 6,555,313; 6,582,915; and 6,593,081).

The monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

The monoclonal antibodies described herein also include "human" antibodies, which can be isolated from various sources, including, e.g., from the blood of a human patient or recombinantly prepared using transgenic animals. Examples of such transgenic animals include KM-MOUSE® (Medarex, Inc., Princeton, N.J.) which has a human heavy chain transgene and a human light chain transchromosome (see WO 02/43478), XENOMOUSE® (Abgenix, Inc., Fremont Calif.; described in, e.g., U.S. Pat. Nos. 5,939,598; 6,075,181; 6,114,598; 6, 150,584 and 6,162, 963 to Kucherlapati et al.), and HUMAB-MOUSE® (Medarex, Inc.; described in, e.g., Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6:

579-591; and Fishwild, D. et al. (1996) Nature Biotechnology 14: 845-851, U.S. Pat. Nos. 5,545,806; 5,569,825; 5,625,126; 5,633,425; 5,789,650; 5,877,397; 5,661,016; 5,814,318; 5,874,299; and 5,770,429; 5,545,807; and PCT Publication Nos. WO 92/03918, WO 93/12227, WO 94/25585, WO 97/13852, WO 98/24884 and WO 99/45962, WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

EXAMPLES

Materials. All Fmoc amino acids and resins were purchased from Advanced Automated Peptide Protein Technologies (AAPPTEC, Louisville, Ky., UXSA), and Fmoc-Lys(Fmoc) were obtained from Novabiochem (San Diego, Calif., USA). The therapeutic human IgG1 (IgG1) was obtained from Bristol-Myers Squibb (Boston, Mass., USA), and IgG elution buffer was sourced from Thermo Fisher Scientific (Rockford, Ill., USA). All other reagents were obtained from VWR (Radnor, Pa., USA) and used as received without further purification.

Molecular Synthesis. C12-Z33 and 2C8-Z33 immuno-amphiphiles were synthesized using similar methods. In brief, Z33 peptide were first synthesized on the Focus XC automatic peptide synthesizer (AAPPTEC, Louisville, Ky.) using standard 9-fluorenylmethoxycarbonyl (Fmoc) solid phase synthesis protocols. The C12 (or 2C8) alkyl chain was then manually coupled at the N-terminus (after Fmoc removal) of Z33 peptide with lauric acid (or octanoic acid)/HBTU/DIEA at a ratio of 4 (or 8):4:6 relative to the Z33 peptide, shaking overnight at room temperature. Fmoc deprotections were performed using a 20% 4-methylpiperidine in DMF solution for 10 minutes, repeating once. In all cases, reactions were monitored by the ninhydrin test (Anaspec Inc., Fremont, Calif.) for free amines. Completed peptides were cleaved from the solid support using a mixture of TFA/TIS/H$_2$O in a ratio of 92.5:5:2.5 for 2.5 hours. Excess TFA was removed by rotary evaporation and cold diethyl ether was added to precipitate the crude peptide. By centrifugation method, precipitated peptide and diethyl ether were separated at 6000 rpm for 3 minutes. Peptides were washed another 2 times with diethyl ether and solution was removed by centrifugation.

The IAs were purified by preparative RP-HPLC using a Varian Polymeric Column (PLRP-S, 100 Å, 10 µm, 150×25 mm) at 25° C. on a Varian ProStar Model 325 preparative HPLC (Agilent Technologies, Santa Clara, Calif.) equipped with a fraction collector. A water/acetonitrile gradient containing 0.1% v/v TFA was used as eluent at a flow rate of 20 ml/min. The absorbance peak was monitored at 220 nm for Z33 peptide segments. The crude materials were dissolved in 20 ml of 0.1% aqueous TFA, and each purification run was carried out with a 10 ml injection. Collected fractions were analyzed MALDI-ToF (BrukerAutoflex III MALDI-ToF instrument, Billerica, Mass.) and those containing the desired product were lyophilized (FreeZone −105° C. 4.5 L freeze dryer, Labconco, Kansas City, Mo.) and stored at −30° C.

Self-Assembly of Immuno-Amphiphiles and TEM Imaging. Immuno-amphiphiles with 1 mM concentration were pretreated with HFIP and then dissolved in 1×PBS or deionized water and aged overnight at room temperature; 10 µl of 10 fold diluted sample was spotted on a carbon film copper grid with 400 square mesh (from EMS: Electron Microscopy Sciences) and the excess was removed with filter paper to leave a thin film of sample on the grid. After letting the sample dry for 5 minutes, 10 µl of 2% uranyl acetate was added to sample grid, and the excess was removed after 30 seconds. All samples were dried for at least 3 hours before TEM imaging.

Circular Dichroism Spectroscopy (CD). The CD experiments of both self-assembled samples were conducted on a Jasco J-710 spectropolarimeter (JASCO, Easton, Md., USA) using a 1 mm path length quartz UV-Vis absorption cell (ThermoFisher Scientific, Pittsburgh, Pa., USA) at 25° C. The samples were instantly diluted from the 1 mM stock solution to 100 µM in 1×PBS prior to the experiment. The spectra were collected in the wavelength range of 190-280 nm as the average of three scans. A background spectrum of the solvent was acquired and subtracted from the sample spectrum. Collected data was normalized with respect to sample concentration.

ITC Experiment. Isothermal titration calorimetry experiments were performed using a high precision VP-ITC titration calorimetric system (Microcal Inc.). The IgG1 solution was titrated with immuno-amphiphiles in 1×PBS (pH 7.4 or 2.8) at 15° C. The IgG1 concentration was calculated using the mass extinction coefficient of 1.4 at 280 nm for a 0.1% (1 mg/ml) IgG solution. The concentration of immuno-amphiphles was determined by total nitrogen assay (*Anal. Biochem.*, 61.2 (1974): 623-627). The heat evolved after each injection was obtained from the integral of the calorimetric signal. The heat associated with the binding of immuno-amphiphiles to IgG1 was obtained by subtracting the heat of dilution. Analysis of the data was performed using MicroCal Origin™ package.

Example 1

Molecular Design of full length Z33 immuno-amphiphiles. The construction of this amphiphilic peptide conjugates such as peptide amphiphiles, peptide-polymer conjugates, peptide-drug conjugates, etc., has been widely used to create a variety of supramolecular nanostructures. IgG binding immuno-amphiphiles consisting of hydrophilic Z33 peptide sequence (FNMQQQRRFYEALHDPNLNEEQRNAK-IKSIRDD) (SEQ ID NO: 1) and hydrophobic alkyl chains were designed to serve as the building motifs for immuno-fibers (IFs). Z33 peptide is a two-helix derivative from protein A (FIG. 1A) that specifically binds to the Fc portion of IgG with high binding affinity (Kd=43 nM).[28, 41-42]

Two IAs, C12-Z33 and 2C8-Z33 (FIG. 1B), were synthesized via directly conjugating a lauric acid moiety (C12), or two octanoic acid moieties (2C8), onto the N-terminus of Z33 peptide. As is shown in FIG. 1C, the IAs were expected to self-assemble into IFs and specifically bind to IgG from the antibody mixture solution. Pure Z33 peptide was also synthesized to compare the bioactivity between Z33 molecule and Z33 containing IFs. Another control molecule C12-SZ33 was designed by conjugating C12 on to the N-terminus of Z33 with scrambled sequence. All the molecules were synthesized and purified using automated solid-phase peptide synthesis (SPPS) methods and RP-HPLC. The purity and expected molecular masses of the synthesized compounds were confirmed using analytical HPLC and mass spectrometry.

Example 2

Figures 2A, 2B, 2C, 2D, 2E, 2F:
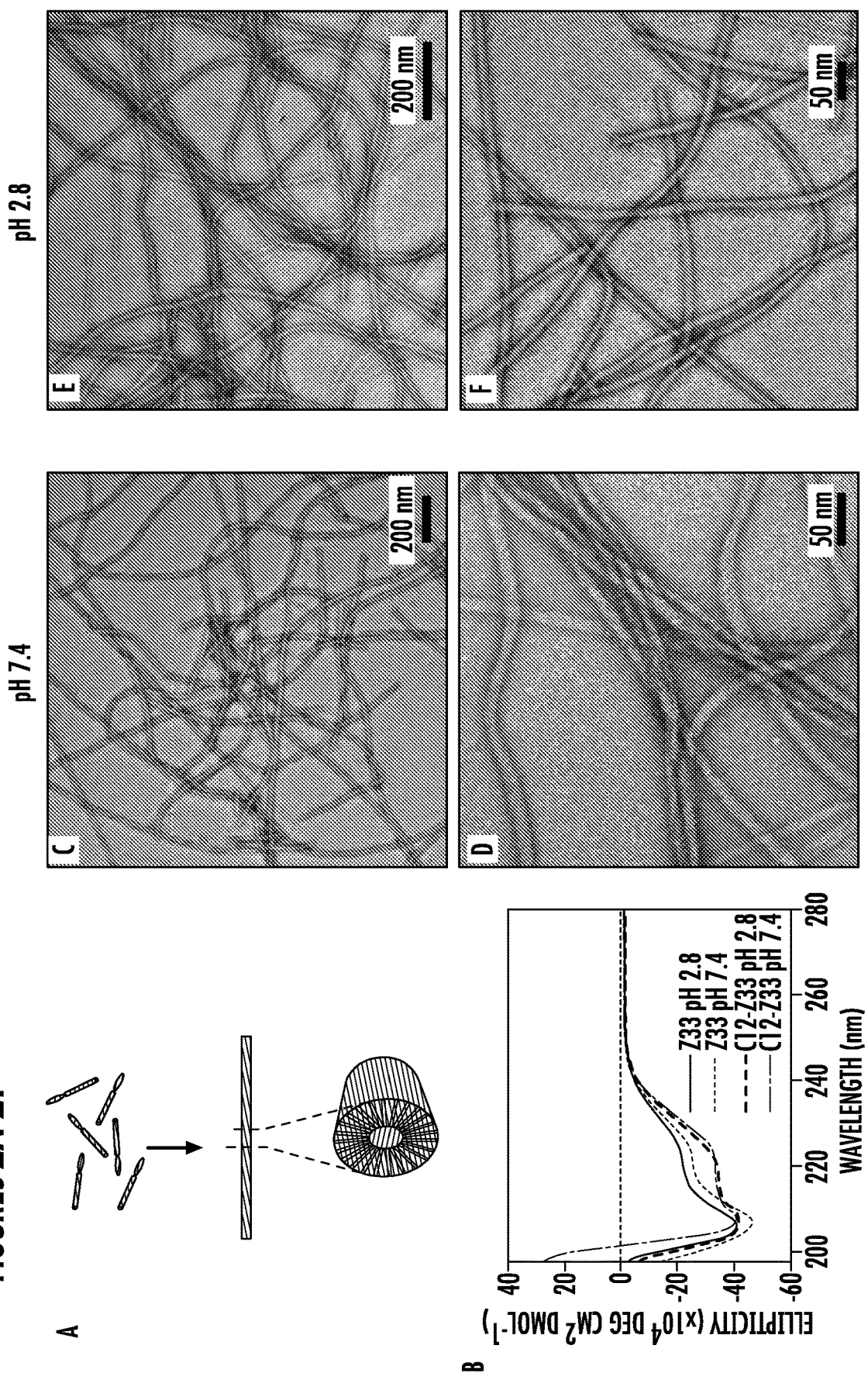
FIGS. 2A-2F. (A) Schematic illustration of self-assembly of C12-Z33. (B) Normalized CD Spectra of Z33 peptide and Z33-C12 at pH 7.4 and 2.8, respectively. TEM characterization of C12-Z33 at pH 7.4 (C, D) and 2.8 (E, F). The TEM samples were prepared at concentration of 100 μM in PBS (pH 7.4) and IgG elution buffer (pH 2.8) separately. The TEM samples were negatively stained with 2 wt % uranyl acetate.
Figures 4A, 4B, 4C, 4D, 4E:
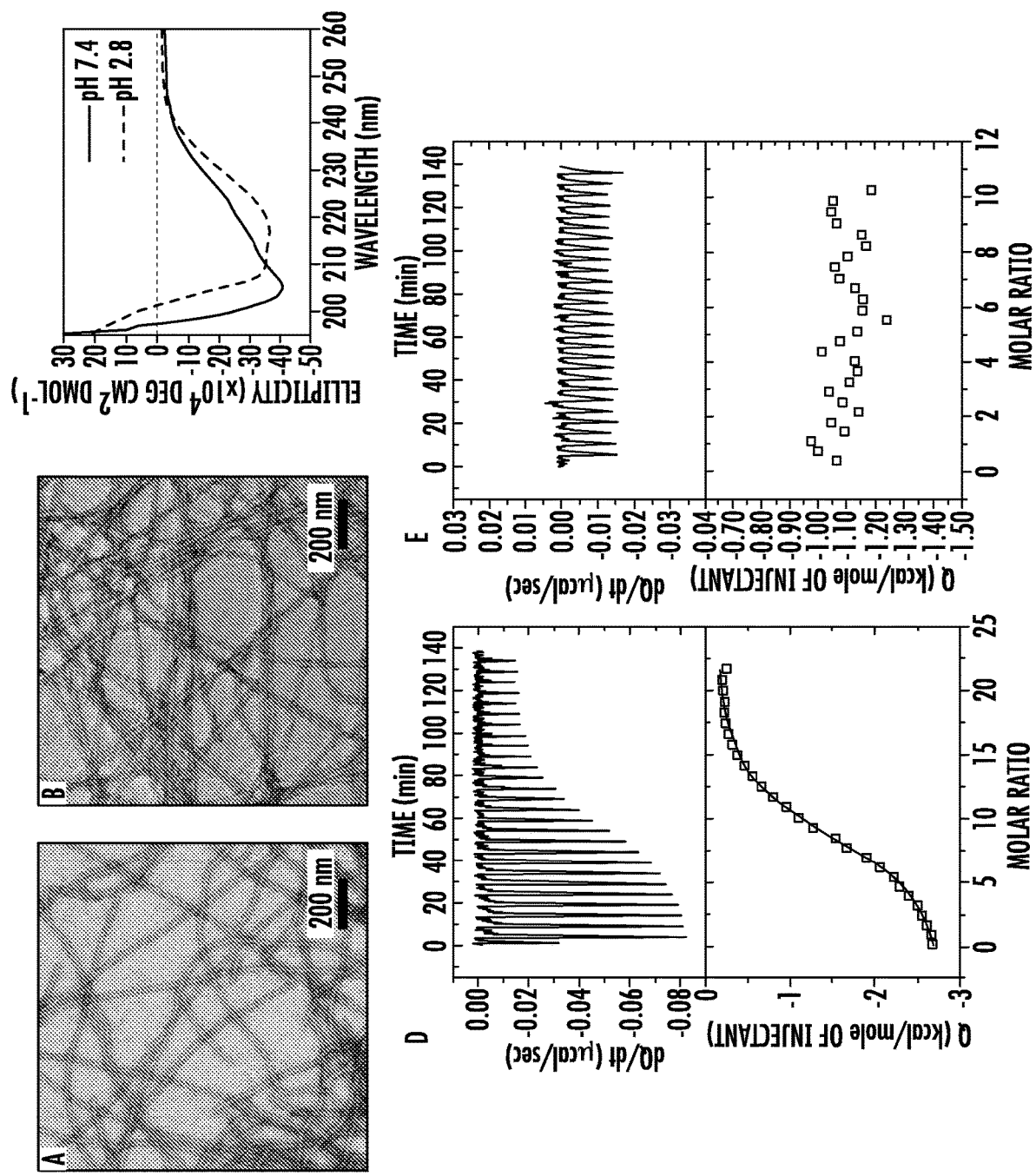
FIGS. 4A-4E. TEM characterization of 2C8-Z33 in (A) PBS at pH 7.4 with a diameter of 16.8±1.5 nm and (B) IgG elution buffer at pH 2.8 with a diameter of 17.3±1.9 nm. The preparation of TEM sample was similar with that of C12-Z33. (C) Normalized CD spectra of 100 μM 2C8-Z33 in PBS at pH 7.4 showed α-helix secondary structures. ITC profiles for the titration of 100 μM 2C8-Z33 into a solution of 2 μM IgG1 in (D) PBS buffer, pH 7.4 and (E) IgG elution buffer, pH 2.8.

Molecular Self-Assembly and Characterization of full length Z33 immuno-amphiphile embodiments. The selfassembly of two IAs can be easily achieved through a two-step operation. First, the IAs were pretreated in hexafluoroisopropanol (HFIP) separately to eliminate any pre-existing nanostructures that may affect its solubility and the uniformity of the self-assembled morphologies. Second, HFIP was removed via evaporation, followed by subsequent addition of deionized water or phosphate-buffered saline (PBS) to reach a final concentration of 1 mM. The IFs formed with alkyl segment trapped in the core of the IFs by hydrophobic interactions and the bioactive Z33 sequence displayed in the shell facing towards the solvent (FIG. 2A). After aging overnight at room temperature, transmission electron microscopy (TEM) and circular dichroism (CD) were utilized to characterize the morphology of the assembled nanostructures.

Given the vital role of pH conditions in the inventive IgG purification methods, the self-assembly behavior of C12-Z33 in response to pH variations was evaluated. Generally, a neutral pH is normally used as the binding condition, while acidic pH is used to elute antibodies from the protein A affinity column.[32, 34] To study the self-assembly behavior at neutral and low pH, PBS (pH 7.4) and IgG elution buffer (pH 2.8) were utilized as the aqueous environment for the self-assembly of C12-Z33. The morphologies of C12-Z33 IFs at different pH were studied by TEM (FIG. 2C through 2F) and CD (FIG. 2B). It was found that the C12-Z33 molecule could be well-dissolved and self-assemble into nanofibers in both the pH conditions mentioned above. Representative TEM images from a solution of 100 μM C12-Z33 revealed that C12-Z33 self-assembled into nanofibrous structure under both physiological condition and acidic condition with a diameter of 16.0±1.7 nm, a value that is less than the length of the fully extended peptide molecule (about 22.5 nm in β-sheet conformation). The length of the nanofibers was shown in micro-meter scale and could not be well-controlled. To further understand the molecular packing within the self-assembled structures, circular dichroism (CD) was used to study the peptide secondary structure. Strong negative signals at around 222 nm (n-π*) and 208 nm (π-π*) were observed in C12-Z33, suggesting the formation of α-helix secondary structure of Z33 segment in the self-assembled state as was shown in the pure Z33 peptide. Based on the CD spectra and the measured diameter of IFs, it is rational to infer the peptides maintained their α-helix secondary structure when packing into IFs. It is worth noting that although CD spectra for C12-Z33 in PBS solution or IgG elution buffer only maintained partial α-helix signals, the ellipticity of the two negative peaks at around 222 nm and 208 nm changed compared with Z33 peptide in the same buffer. The shift of the CD spectra may result from the formation of the IFs that can change the molecular packing of Z33 segment from its free state and may subsequently influence its binding affinity to IgG due to the specific conformation required for the binding sites.

Example 3

ITC Experiment for Measuring Binding Affinity of IFs. Given the conformation change in the secondary structure of Z33 peptide after incorporation into IFs, it is of great interest to know if the formation of C12-Z33 IFs would influence the IgG binding ability existing in original Z33 peptide. To investigate the binding affinity of the self-assembled C12-Z33 IFs, thermodynamic properties of the binding to IgG1 were investigated by isothermal titration calorimetry (ITC). ITC has been widely employed to monitor the binding events between great numbers of proteins and ligands,[43-45] which is an excellent method to explore if the binding could occur between C12-Z33 IFs and IgG1.[46-47] The heat that is associated with the binding reaction was recorded during the stepwise injections and the thermodynamic parameters including thermodynamic dissociation constant ($K_d$), molar enthalpy change ($\Delta H°$), and stoichiometry (N), can be obtained directly.[44]

TABLE 1

Thermodynamic parameters for binding of Z33-based ligands to IgG1 at 15° C. in phosphate-buffer saline at pH 7.4. Data are reported per ligand.

| Ligands | $K_d$ (nM) | $\Delta G°$ (kcal · mol$^{-1}$) | $\Delta H°$ (kcal · mol$^{-1}$) | $-T\Delta S°$ (kcal · mol$^{-1}$) | N |
|---|---|---|---|---|---|
| Z33 | 60 | −9.5 | −23.1 | 13.6 | 2.31 |
| C12-Z33 | 650 | −8.1 | −9.3 | 1.2 | 3.10 |
| 2C8-Z33 | 1115 | −7.8 | −2.8 | −5.0 | 9.13 |

TABLE 2

Thermodynamic parameters for binding of Z33-based ligands to IgG1 at 15° C. in phosphate-buffer saline at pH 7.4. Data are reported per IgG1.

| Ligands | $K_d$ (nM) | $\Delta G°$ (kcal · mol$^{-1}$) | $\Delta H°$ (kcal · mol$^{-1}$) | $-T\Delta S°$ (kcal · mol$^{-1}$) |
|---|---|---|---|---|
| Z33 | 26 | −10.0 | −53.4 | 43.4 |
| C12-Z33 | 209 | −8.8 | −28.9 | 20.1 |
| 2C8-Z33 | 122 | −9.1 | −25.9 | 16.8 |

In a typical ITC experiment, a solution of 100 μM C12-Z33 in PBS buffer was aged overnight and then injected into a solution of 2 μM IgG1 in the same buffer at 15° C., pH 7.4. Typical thermograms and binding isotherms were shown in FIG. 3A and the thermodynamic parameters reported per ligand are summarized in Table 1. The ITC results for the binding of C12-Z33 IFs to IgG1 revealed an enthalpy driven binding event characterized by a $K_d$ of 650. To further compare the binding efficiency of C12-Z33 IFs, we synthesized the Z33 peptide which was proved to bind tightly to IgG1 with a $K_d$ of 43 nM measured by surface plasmon resonance. The binding properties of Z33 peptide to IgG1 was measured by ITC at 15° C. in PBS, pH 7.4 and typical thermograms and binding isotherms were shown in FIG. 3C. In addition to a 100-fold better affinity, the stoichiometry for Z33 was 2.3, whereas the apparent stoichiometry for C12-Z33 was 3.1, indicating that not all the C12-Z33 in IFs were available for the binding to IgG1 molecule. The efficiency of C12-Z33 molecule that is able to bind to IgG1 can be estimated to be 74.2% by dividing the stoichiometry of Z33 by that of C12-Z33.

While normalization per ligand allows the determination of the apparent stoichiometry of binding, comparison of the thermodynamic parameters should be done after normalization per mole of IgG as shown in Table 2. The binding of Z33 to IgG was characterized by a large favorable enthalpy opposed by a large unfavorable entropy change. The thermodynamic signature for the binding of C12-Z33 was similar although the magnitudes of the enthalpy and entropy changes were smaller. Although C12-Z33 binds with a less unfavorable entropy than Z33, the loss in favorable enthalpy is even larger which results in an overall lower binding affinity. An overall loss in the favorable binding enthalpy could possibly be caused by the unfavorable enthalpy associated with the disruption of the IFs. There is also a possibility that favorable interactions with IgG1 are limited due to restrictions in the IFs. Titration of IgG1 with C12-Z33 were also performed in IgG elution buffer (pH 2.8) at 15° C. (FIG. 3B) in order to demonstrate significantly lower binding affinity at this low pH suitable for elution from the IFs.

To exclude the non-specific binding between IFs and IgG1, C12-SZ33 with scrambled Z33 peptide sequence was used as negative control. This C12-SZ33 IAs shows similar self-assembly properties and secondary structures characterized with TEM and CD (data not shown). ITC experiment was carried out by injecting 100 μM C12-SZ33 IAs into 2 μM IgG1 solution at 15° C. in PBS at pH 7.4 to measure their binding ability. The thermograms and binding isotherms in FIG. 3D suggests specific interactions between IgG1 and the Z33 peptide.

Example 4

To further prove the universality of the function of IFs, double chain alkylated IAs 2C8-Z33 were also studied from self-assembly property to binding affinity to IgG1 (FIGS. 4A-E). Nanoscale IFs with uniform diameters were observed in TEM image and α-helix secondary structure was confirmed by CD. From the ITC results, binding between 2C8-Z33 and IgG1 occurred at 15° C. in PBS, pH 7.4, whereas no detectable binding occurred in elution buffer, pH 2.8. The apparent stoichiometry for the binding of 2C8-Z33 was 9.1, indicating an even lower efficiency of binding. Although 2C8-Z33 binds with a less favorable enthalpy of binding than C12-Z33, the contribution from the entropy is less unfavorable, which results in binding affinity that is slightly better (Table 2). From the results discussed above, we demonstrated that with the high density of binding sites displayed on the surface, the self-assembled IFs are able to maintain favorable binding ability to IgG1 as was shown in the original Z33 peptide. There is nevertheless a loss in overall binding affinity observed for the IFs, which is of enthalpic origin. The loss in favorable enthalpy can be explained by loss of interactions due to restrictions in the IFs and an unfavorable enthalpy contribution associated with the disruption of the particles. The molecular level packing within IFs determines their morphological as well as functional properties that can greatly affect their performance in bioactivity.

Example 5

Potential Applications for Purification of IgG molecules.

Figures 5A, 5B, 5C, 5D:
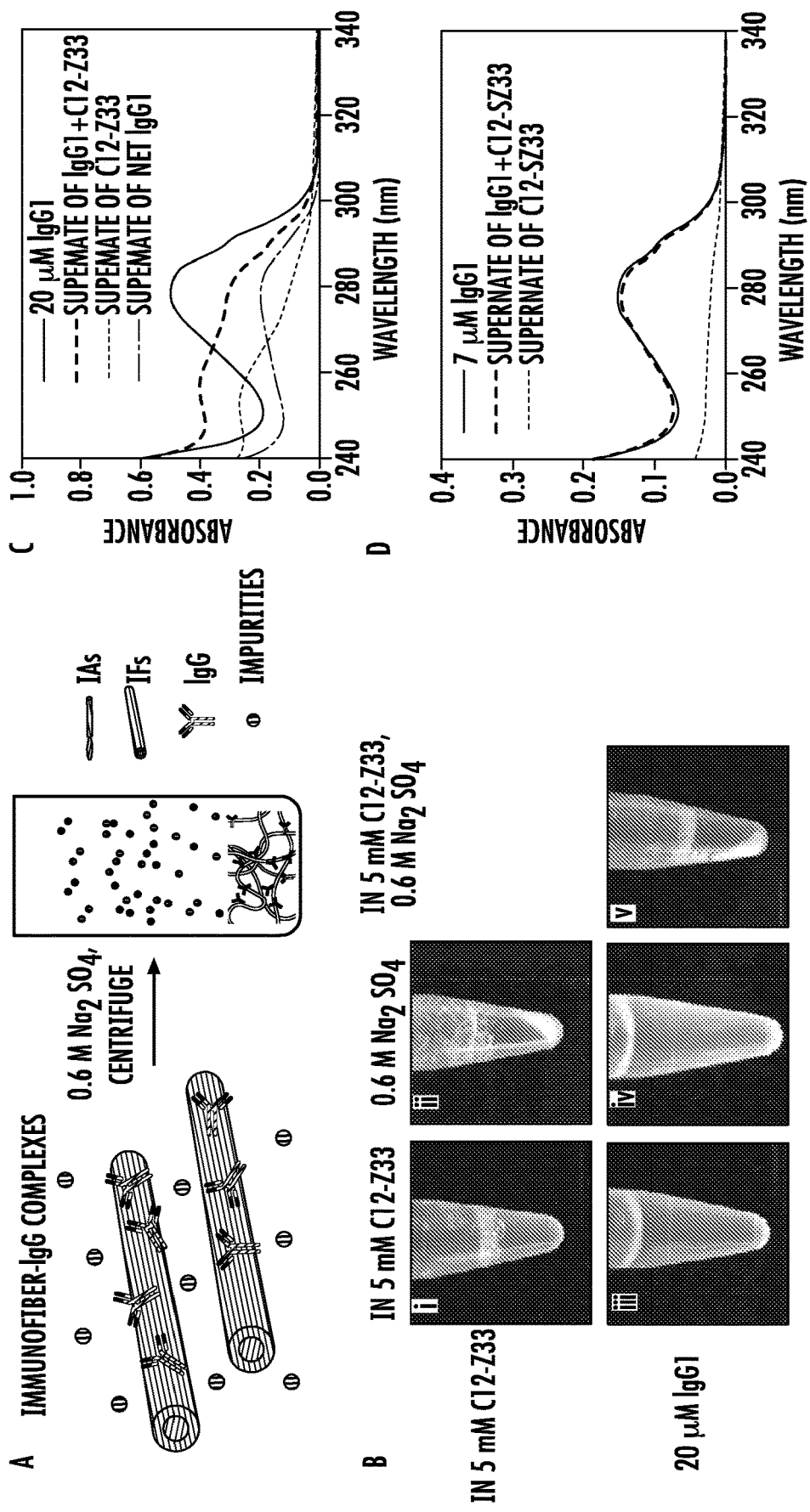
FIGS. 5A-5D. Schematic illustration of the precipitation of IFs-IgG complexes triggered by 0.6 M $Na_2SO_4$ solution. (B) Photographs of 5 mM PBS solution of C12-Z33 (i) before and (ii) after addition of 0.6 M $Na_2SO_4$ and 20 μM PBS solutions of IgG1 with (iii) 5 mM C12-Z33, (iv) 0.6 M $Na_2SO_4$, and (v) 5 mM C12-Z33 and 0.6 M $Na_2SO_4$. Precipitation were observed in (ii) and (v). (C) Absorbance spectra of C12-Z33 and IgG1+C12-Z33 complexes before and after addition of 0.6 M $Na_2SO_4$. The supernatant of net IgG1 is derived from the supernatant of IgG1+C12-Z33 subtracted by the supernatant of C12-Z33. (D) Absorbance spectra of 2 mM C12-SZ33 and IgG1+C12-SZ33 complexes before and after addition of 0.6 M $Na_2SO_4$.

The diversity of constituent amino acids provides a broad basis for non-covalent interactions including hydrogen bonding, π-π stacking, hydrophobic collapse, and electrostatic interactions between self-assembling peptide nanofibers. For example, the solubility of acidic and basic amino acids is determined by the degree of ionization, a property that is pH and ionic strength dependent. The self-assembly process of charged peptides can thus be facilitated by tuning the pH or adding salts to reduce the electrostatic repulsions, promote aggregation and even precipitation. Considering the numerous charged amino acid residues displayed in Z33 peptide, a fascinating advantage of the inventive immunofiber system of the present invention relies in the easily-tunable solubility. Once the IgG is bound to IFs, the IgG-IFs complexes are of high potential to be precipitated out by adding salts with high ionic intensity (FIG. 5A).

C12-Z33 IFs were chosen to study the possibility to precipitate IgG1 because of its relatively high binding affinity to IgG1. As shown in FIG. 5B (i-ii), 5 mM C12-Z33 could be well dissolved in PBS solution but precipitated in a PBS solution of 0.6 M $Na_2SO_4$. The zeta potential of C12-Z33 in PBS solution is −7.61 mV and the addition of $Na_2SO_4$ could screen the charges on the surface of IFs and thus induce precipitation. For IgG1, it is well dissolved in 5 mM C12-Z33 as well as 0.6 M $Na_2SO_4$. However, precipitation was observed after mixing 20 μM IgG1 and 5 mM C12-Z33 for 5 minutes followed by addition of 0.6 M $Na_2SO_4$. To determine composition of the precipitates, two parallel experiments were carried out. 5 mM C12-Z33 in 0.6 M $Na_2SO_4$ was centrifuged and ultraviolet-visible (UV-Vis) spectroscopy was used to monitor the absorbance changes of supernatants at 280 nm before and after the addition of $Na_2SO_4$. Same procedures were conducted on a mixture of 5 mM C12-Z33 and 20 μM IgG1 in 0.6 M $Na_2SO_4$. As is shown in FIG. 5C, most C12-Z33 IFs were able to be precipitated out by 0.6 M $Na_2SO_4$. For IgG1-IF complex system, the absorbance at 280 nm was reduced to a level below the initial absorbance of IgG1, indicating the removal of IgG1 from the solution. More clearly, the absorbance of supernatants of net IgG1 was plotted via subtracting the value of green line from the blue line, suggesting more than 60% IgG1 was removed from the supernatant. So far, the possibility of our IFs to serve as a new affinity precipitation agent was preliminary proved.

Example 6

Confirmation of IgG binding to the IFs of the present invention.

Figure 6A:
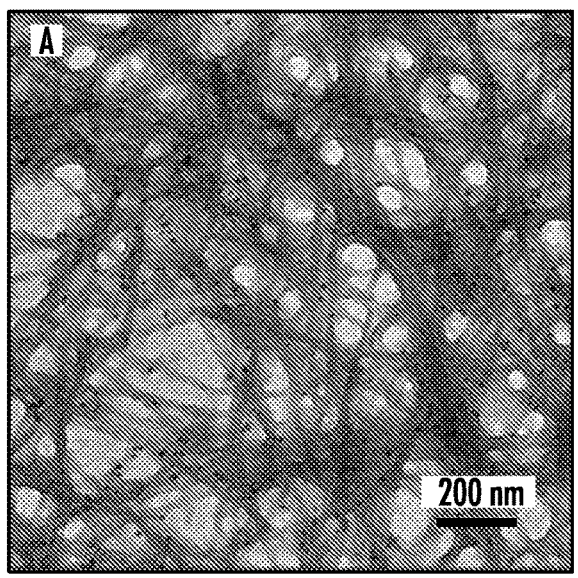
FIGS. 6A-6D. TEM images of (A, C) 100 μM C12-Z33 and (B, D) 100 μM C12-SZ33 after incubation with IgG-coated Au nanoparticles in PBS, pH 7.4. IgG concentration: 0.33-0.66 μM.
Figure 6B:
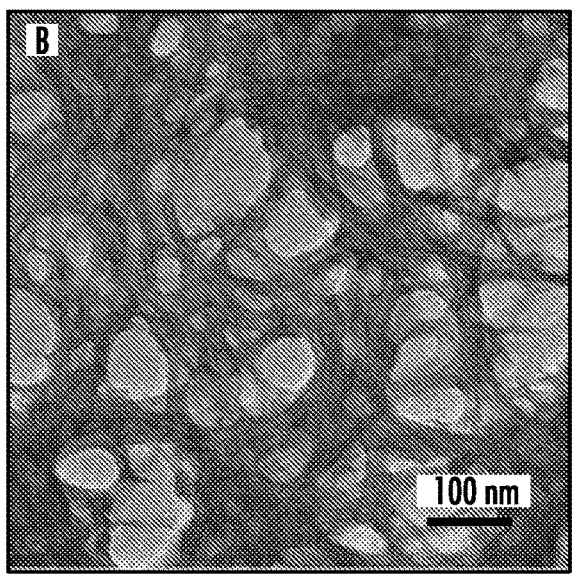
Figure 6C:
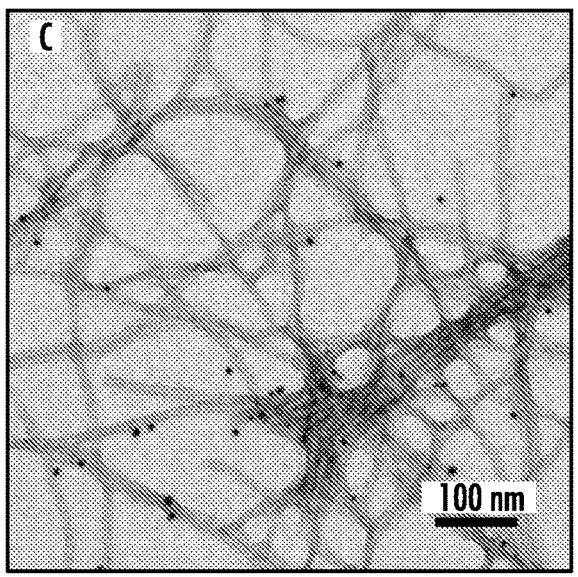
Figure 6D:
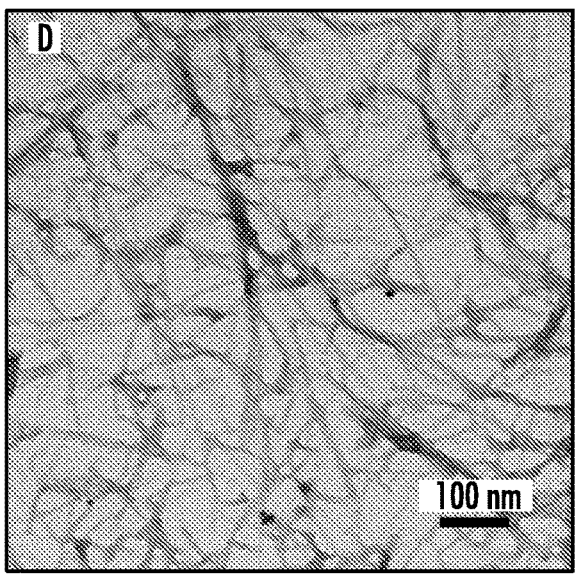
Figure 7:
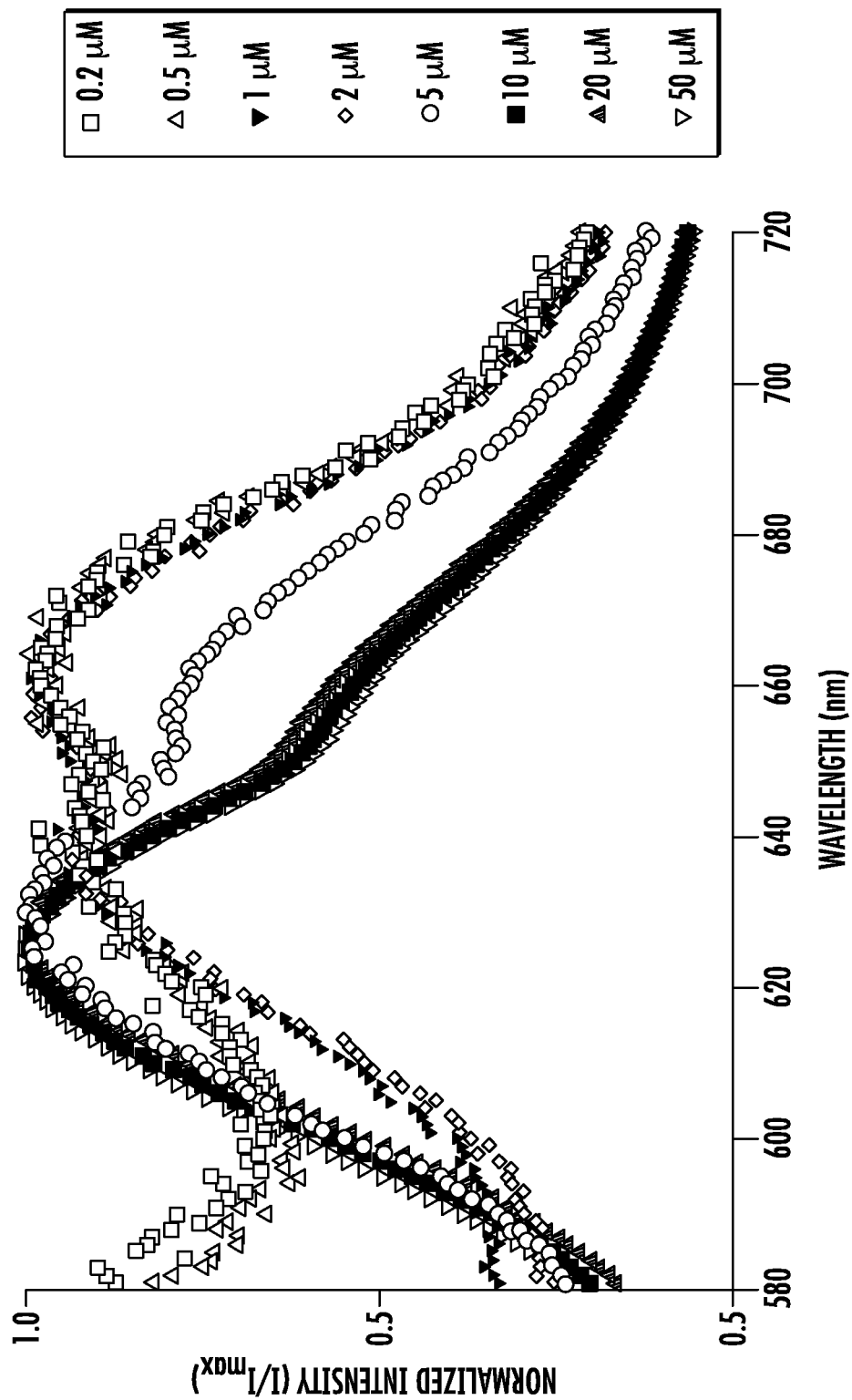
FIG. 7. CMC Measurement of C12-Z33. Emission spectra of the reporter dye Nile Red monitored by a Fluorolog fluorometer (Jobin Yvon, Edison, N.J.) after incubated with a series of concentrations of C12-Z33. Excitation wavelength was fixed at 560 nm; emission spectra were monitored 580-720 nm. The CMC of C12-Z33 is determined by a blue-shift of the emission maximum, where the transition indicates the dye partitioning into the hydrophobic compartment of assembled nanostructures. All spectra shown here are normalized by the emission maximum. The CMC range for C12-Z33: 2-5 μM.

The difficulty to identify the IgG structure in TEM limited the visualization of binding between immunofibers and IgG directly. To confirm that the IgG is present on the surface of the immunofibers, the preformed C12-Z33 and C12-SZ33 immunofibers were incubated with 10 nm IgG-labelled Au nanoparticles for 2 h separately. After placing a drop of each solution onto a TEM grid, the grid was blotted with a filter paper and left to dry naturally. Then, we carefully washed the grid 3 times with PBS buffer, in an effort to remove the unbounded Au nanoparticles before staining the sample with uranyl acetate. TEM images of C12-Z33 incubated with IgG-coated Au nanoparticles in both dense and sparse (FIGS. 6A and 6C) areas confirmed the binding of IgG to surfaces of Z33-presenting nanofibers. Very few Au nanoparticles were observed to attach onto the control nanofibers bearing the scrambled Z33 sequence (FIGS. 6B and 6D). This study suggests that the co-localization of C12-Z33 immunofibers and IgG-coated Au nanoparticles is indeed a result of specific binding. It should be noted that the density of Au nanoparticles was relatively low on the long immunofibers, likely due to the limited accessibility of the tight packing of Z33 immuno-amphiphiles after their self-assembly into nanofibers. Another possibility is that the IgG-coated Au nanoparticles could be bound to the C12-Z33 in the monomer state and then taken away in the washing steps, because the IgG concentration (0.33-0.66 μM) in the IgG-coated Au nanoparticles was below the critical micelle concentration value for C12-Z33, which is 2-5 μM (FIG. 7).

Example 7

Visualization of IgG interactions with the IFs of the present invention.

Figures 8A, 8B:
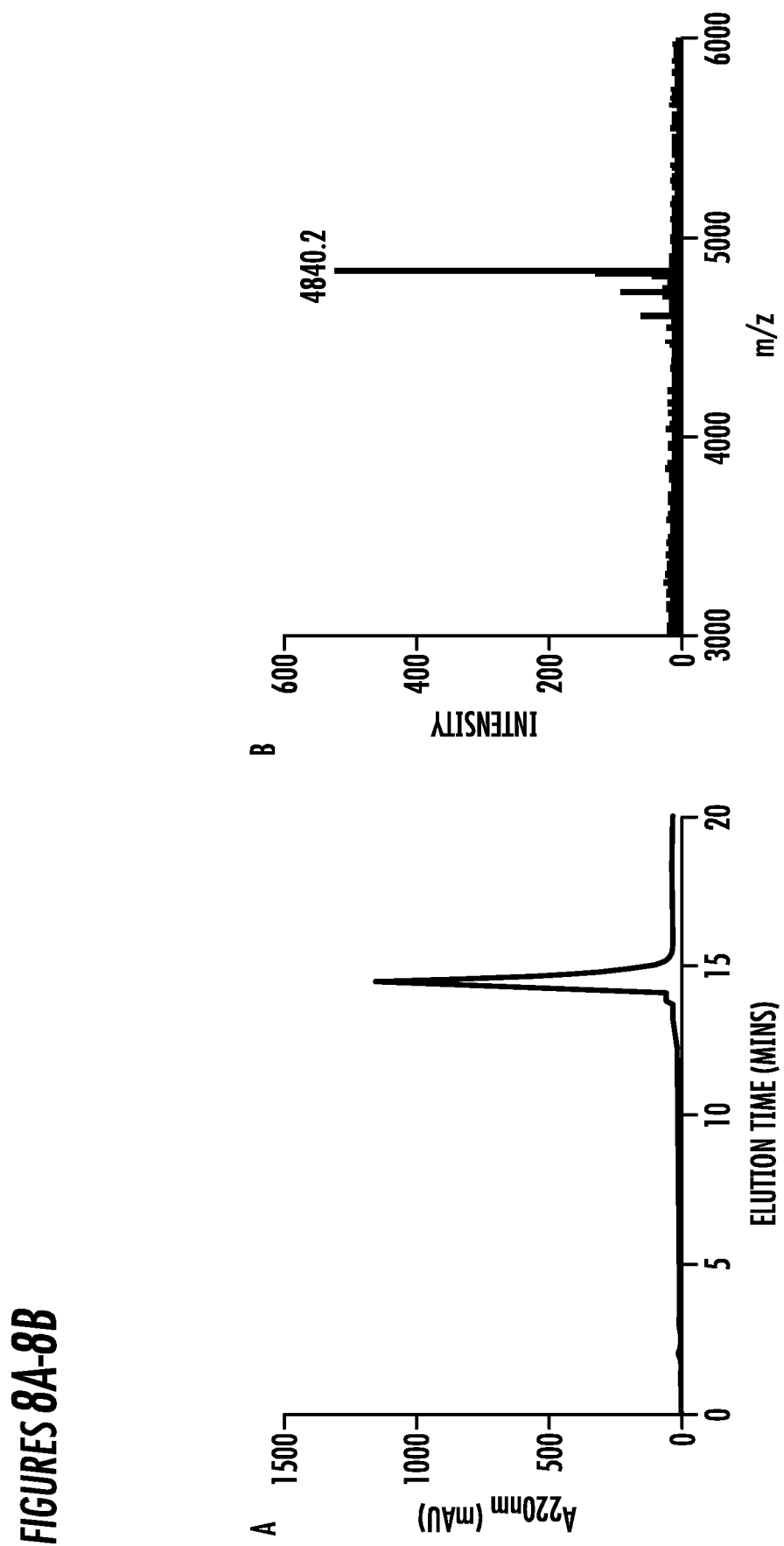
FIGS. 8A-B. RP-HPLC (8A) and MALDI-TOF MS (8B) characterization of RB-C12-Z33. The RP-HPLC spectrum confirms the purity of the product (>99%). The expected mass is 4838.5. The peak at 4840.2 corresponds to [M+H]$^+$.
Figures 9A, 9B, 9C, 9D:
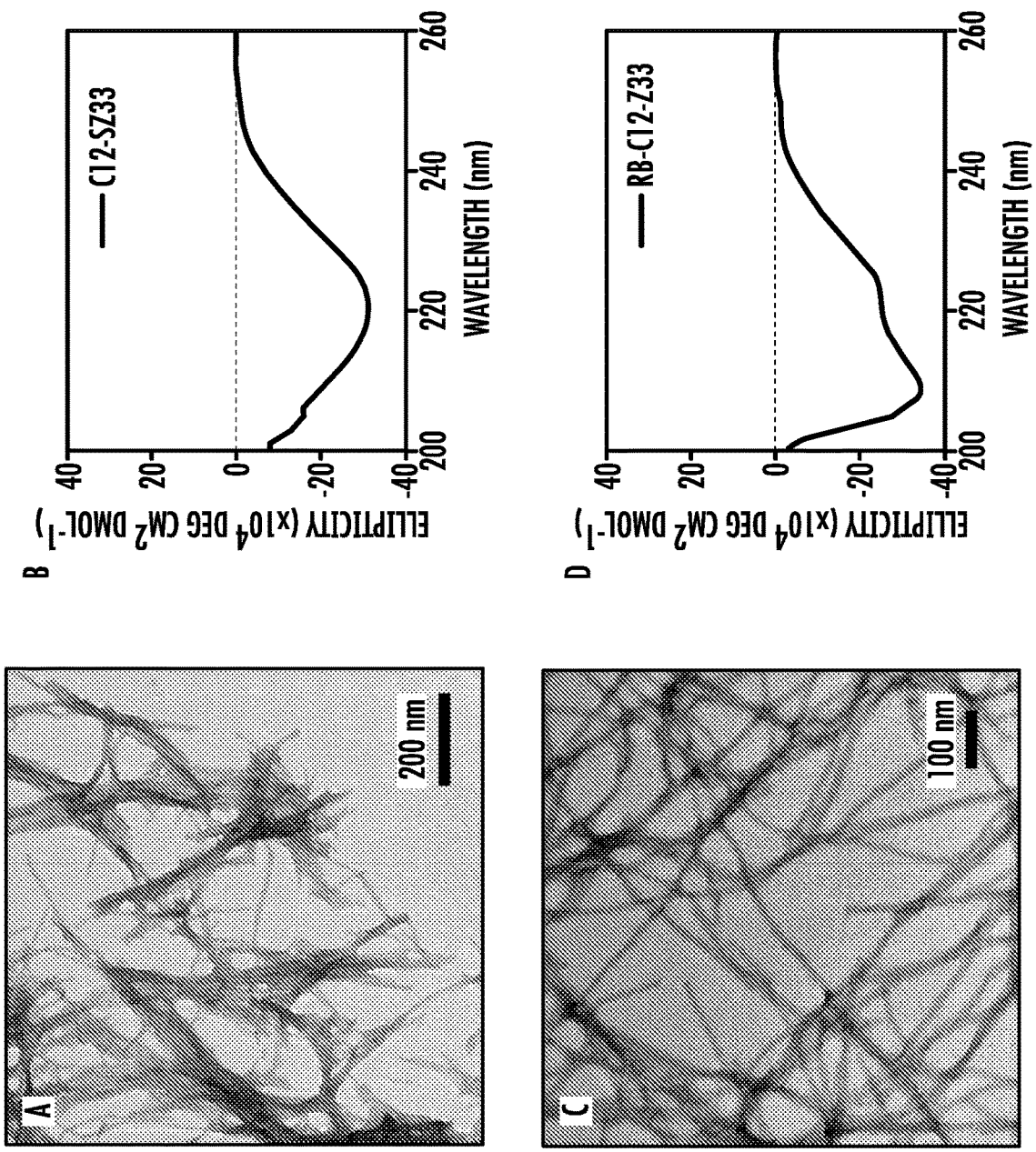
FIGS. 9A-D. TEM images of 100 μM (9A) C12-SZ33 and (9C) RB-C12-Z33 in PBS, pH 7.4. Both molecules self-assembled into nanofibers with diameters of 11.5±1.5 nm and 13.8±1.8 nm respectively. Normalized CD spectra of 100 μM (9B) C12-SZ33 and (9D) RB-C12-Z33 nanofibers in PBS at pH 7.4 showed β-sheet and α-helix conformation, respectively.
Figures 10A, 10B, 10C:
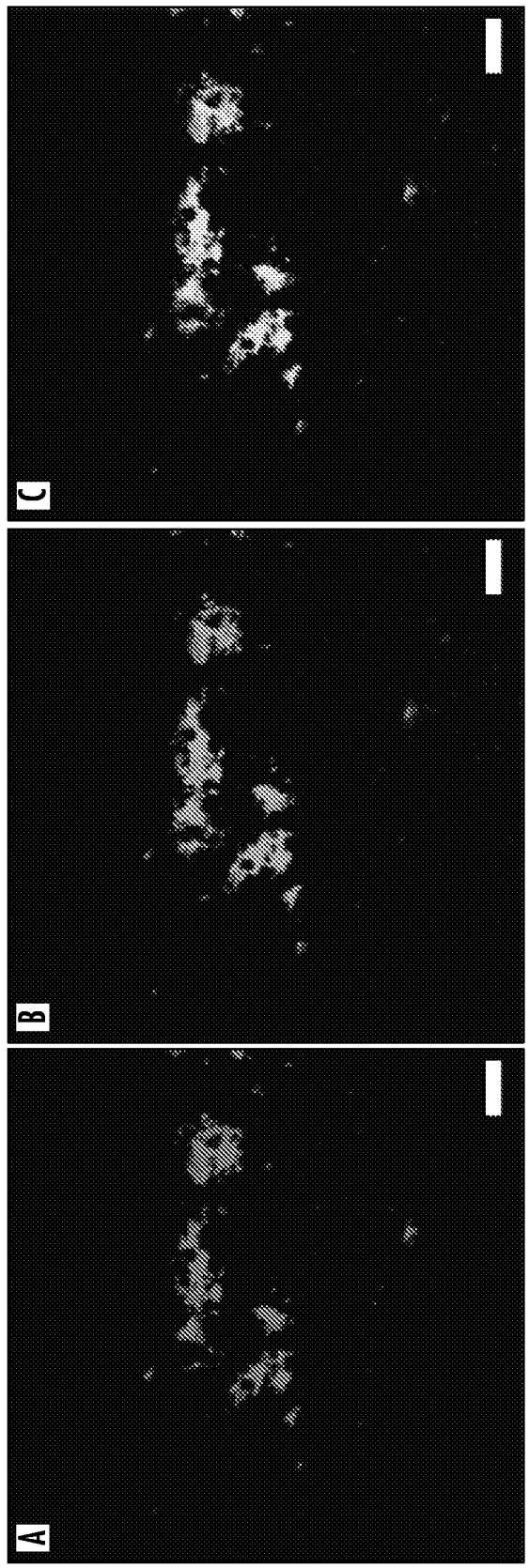
FIGS. 10A-C. Confocal fluorescence images of 100 μM RB-C12-Z33 incubated with 2 μM FITC-IgG in PBS (pH 7.4) show co-localization of the fluorescence signal of Rhodamine B with that of the FITC. (A) Image of Rhodamine B fluorescence. (B) Image of FITC fluorescence and (C) merged image of (A) and (B). Scale bar: 20 μm.

To better visualize the interactions between C12-Z33 immunofibers and IgG, labelling the C12-Z33 with the fluorescent dye (Rhodamine B) allows for direct imaging of fluorescent immunofibers and FITC-IgG under a confocal laser scanning microscope. Rhodamine B has been extensively used for staining biomaterials. Rhodamine B labelled C12-Z33 (RB-C12-Z33) was synthesized by adding a lysine at the N-terminal of Z33 (FIG. 8) Rhodamine B and C12 were conjugated to the amine group on the side chain and backbone of the newly added lysine separately. It was assumed that the fluorescent labelling will not interfere with the binding ability of C12-Z33 because the dye will stay in the hydrophobic core after self-assembling into the immunofibers together with the C12 and it's located remotely from the binding sequence Z33. The self-assembled fibrous morphology in PBS was confirmed using TEM (FIG. 9C). 100 µM RB-C12-Z33 diluted from a 1 mM stock solution and 2 µM FITC-IgG were premixed in PBS. 30 µl solution was spotted on a clean microscope slide right before imaging and covered by a coverslip to obtain a thin layer of liquid. Fluorescence images (FIGS. 10A-C) were then taken by a confocal laser scanning microscope and showed co-localization of fluorescence signals from both RB-C12-Z33 (red) and FITC-IgG (green). It was found that FITC-IgG formed large bright assemblies that were never observed in the pure FITC-IgG solution and the solution incubated with C12-SZ33 at same conditions (data not shown). Compared to the bright fluorescence of FITC-IgG when incubated with RB-C12-Z33, low fluorescent signals were detected in the PBS solution or after incubated with C12-SZ33. This showed that FITC-IgG was dispersed well in the PBS buffer or in the presence of C12-SZ33, while the binding between RB-C12-Z33 and FITC-IgG induced the aggregation of FITC-IgG and the strong fluorescence.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Altunbas, A.; Lee, S. J.; Rajasekaran, S. A.; Schneider, J. P.; Pochan, D. J., Encapsulation of curcumin in self-assembling peptide hydrogels as injectable drug delivery vehicles. Biomaterials 2011, 32 (25), 5906-14.
2. Chow, L. W.; Wang, L. J.; Kaufman, D. B.; Stupp, S. I., Self-assembling nanostructures to deliver angiogenic factors to pancreatic islets. Biomaterials 2010, 31 (24), 6154-61.
3. Koutsopoulos, S.; Zhang, S., Two-layered injectable self-assembling peptide scaffold hydrogels for long-term sustained release of human antibodies. J Control Release 2012, 160 (3), 451-8.
4. Lock, L. L.; Reyes, C. D.; Zhang, P. C.; Cui, H. G., Tuning Cellular Uptake of Molecular Probes by Rational Design of Their Assembly into Supramolecular Nanoprobes. Journal of the American Chemical Society 2016, 138 (10), 3533-3540.
5. Cheetham, A. G.; Zhang, P. C.; Lin, Y. A.; Lock, L. L.; Cui, H. G., Supramolecular Nanostructures Formed by Anticancer Drug Assembly. Journal of the American Chemical Society 2013, 135 (8), 2907-2910.
6. Hu, Y.; Lin, R.; Patel, K.; Cheetham, A. G.; Kan, C. Y.; Cui, H. G., Spatiotemporal control of the creation and immolation of peptide assemblies. Coordination Chemistry Reviews 2016, 320, 2-17.
7. Ma, W.; Cheetham, A. G.; Cui, H. G., Building nanostructures with drugs. Nano Today 2016, 11 (1), 13-30.
8. Black, M.; Trent, A.; Kostenko, Y.; Lee, J. S.; Olive, C.; Tirrell, M., Self-Assembled Peptide Amphiphile Micelles Containing a Cytotoxic T-Cell Epitope Promote a Protective Immune Response In Vivo. Adv Mater 2012, 24 (28), 3845-3849.
9. Shimada, T.; Lee, S.; Bates, F. S.; Hotta, A.; Tirrell, M., Wormlike micelle formation in peptide-lipid conjugates driven by secondary structure transformation of the headgroups. The journal of physical chemistry. B 2009, 113 (42), 13711-4.
10. Trent, A.; Marullo, R.; Lin, B.; Black, M.; Tirrell, M., Structural properties of soluble peptide amphiphile micelles. Soft Matter 2011, 7 (20), 9572-9582.
11. Cui, H.; Webber, M. J.; Stupp, S. I., Self-assembly of peptide amphiphiles: from molecules to nanostructures to biomaterials. Biopolymers 2010, 94 (1), 1-18.
12. Hartgerink, J. D.; Beniash, E.; Stupp, S. I., Self-assembly and mineralization of peptideamphiphile nanofibers. Science 2001, 294 (5547), 1684-1688.
13. Niece, K. L.; Hartgerink, J. D.; Donners, J. J.; Stupp, S. I., Self-assembly combining two bioactive peptide-amphiphile molecules into nanofibers by electrostatic attraction. Journal of the American Chemical Society 2003, 125 (24), 7146-7147.
14. Webber, M. J.; Tongers, J.; Renault, M. A.; Roncalli, J. G.; Losordo, D. W.; Stupp, S. I., Development of bioactive peptide amphiphiles for therapeutic cell delivery. Acta Biomater 2010, 6 (1), 3-11.
15. Cui, H. G.; Cheetham, A. G.; Pashuck, E. T.; Stupp, S. I., Amino Acid Sequence in Constitutionally Isomeric Tetrapeptide Amphiphiles Dictates Architecture of One- Dimensional Nanostructures. Journal of the American Chemical Society 2014, 136 (35), 12461-12468.
16. Moyer, T. J.; Finbloom, J. A.; Chen, F.; Toft, D. J.; Cryns, V. L.; Stupp, S. I., pH and Amphiphilic Structure Direct Supramolecular Behavior in Biofunctional Assemblies. Journal of the American Chemical Society 2014, 136 (42), 14746-14752.
17. Webber, M. J.; Tongers, J.; Renault, M.-A.; Roncalli, J. G.; Losordo, D. W.; Stupp, S. I., Reprint of: Development of bioactive peptide amphiphiles for therapeutic cell delivery. Acta biomaterialia 2015, 23, S42-S51.
18. Yu, Y.; Sleep, E.; Stupp, S. I.; Qin, G. J., Novel Bioactive Peptide Amphiphiles Nanofibers for Enhancement of Human Cd34+ Cell Mediated Ischemic Tissue Repair. Circulation 2013, 128 (Suppl 22), A19043-A19043.
19. Arslan, E.; Garip, I. C.; Gulseren, G.; Tekinay, A. B.; Guler, M. O., Bioactive supramolecular peptide nanofibers for regenerative medicine. Advanced healthcare materials 2014, 3 (9), 1357-1376.
20. Kokkoli, E.; Mardilovich, A.; Wedekind, A.; Rexeisen, E. L.; Garg, A.; Craig, J. A., Self-assembly and applications of biomimetic and bioactive peptide-amphiphiles. Soft Matter 2006, 2 (12), 1015.
21. Rudra, J. S.; Sun, T.; Bird, K. C.; Daniels, M. D.; Gasiorowski, J. Z.; Chong, A. S.; Collier, J. H., Modulating adaptive immune responses to peptide self-assemblies. Acs Nano 2012, 6 (2), 1557-1564.
22. Ecker, D. M.; Jones, S. D.; Levine, H. L., The therapeutic monoclonal antibody market. MAbs 2015, 7 (1), 9-14.
23. Low, D.; O'Leary, R.; Pujar, N. S., Future of antibody purification. J Chromatogr B Analyt Technol Biomed Life Sci 2007, 848 (1), 48-63.
24. Shukla, A. A.; Hubbard, B.; Tressel, T.; Guhan, S.; Low, D., Downstream processing of monoclonal antibodies-application of platform approaches. J Chromatogr B Analyt Technol Biomed Life Sci 2007, 848 (1), 28-39.
25. Deisenhofer, J., Crystallographic refinement and atomic models of a human Fc fragment and its complex with fragment B of protein A from *Staphylococcus aureus* at 2.9- and 2.8-. ANG resolution. Biochemistry 1981, 20 (9), 2361-2370.
26. Moks, T.; ABRAHMSÉN, L.; NILSSON, B.; Hellman, U.; SJÖQUIST, J.; Uhlen, M., Staphylococcal protein A consists of five IgG-binding domains. European Journal of Biochemistry 1986, 156 (3), 637-643.
27. Braisted, A. C.; Wells, J. A., Minimizing a binding domain from protein A. Proceedings of the National Academy of Sciences 1996, 93 (12), 5688-5692.
28. Nilsson, B.; Moks, T.; Jonsson, B.; Abrahmsén, L.; Elmblad, A.; Holmgren, E.; Henrichson, C.; Jones, T. A.; Uhlén, M., A synthetic IgG-binding domain based on staphylococcal protein A. Protein engineering 1987, 1 (2), 107-113.
29. Starovasnik, M. A.; Braisted, A. C.; Wells, J. A., Structural mimicry of a native protein by a minimized binding domain. Proceedings of the National Academy of Sciences 1997, 94 (19), 10080-10085.
30. Olszewski, K. A.; Kolinski, A.; Skolnick, J., Folding simulations and computer redesign of protein A three-helix bundle motifs. Proteins 1996, 25.
31. Boutelje, J.; Karlström, A. R.; Hartmanis, M. G.; Holmgren, E.; Sjögren, A.; Levine, R. L., Human immunodeficiency viral protease is catalytically active as a fusion protein: characterization of the fusion and native enzymes produced in *Escherichia coli*. Archives of biochemistry and biophysics 1990, 283 (1), 141-149.
32. Hober, S.; Nord, K.; Linhult, M., Protein A chromatography for antibody purification. J Chromatogr B Analyt Technol Biomed Life Sci 2007, 848 (1), 40-7.
33. Guatrecasas, P., Protein purification by affinity chromatography. J. Biol. Chem 1970, 245 (12), 3050.
34. Huse, K.; Böhme, H.-J.; Scholz, G. H., Purification of antibodies by affinity chromatography. Journal of biochemical and biophysical methods 2002, 51 (3), 217-231.
35. Hassouneh, W.; Christensen, T.; Chilkoti, A., Elastin-like polypeptides as a purification tag for recombinant proteins. Curr Protoc Protein Sci 2010, Chapter 6, Unit 6 11.
36. Sheth, R. D.; Jin, M.; Bhut, B. V.; Li, Z.; Chen, W.; Cramer, S. M., Affinity precipitation of a monoclonal antibody from an industrial harvest feedstock using an ELP-Z stimuli responsive biopolymer. Biotechnol Bioeng 2014, 111 (8), 1595-603.
37. Handlogten, M. W.; Stefanick, J. F.; Alves, N. J.; Bilgicer, B., Nonchromatographic affinity precipitation method for the purification of bivalently active pharmaceutical antibodies from biological fluids. Analytical chemistry 2013, 85 (10), 5271-5278.
38. Eisen, H. N.; Siskind, G. W., Variations in Affinities of Antibodies during the Immune Response*. Biochemistry 1964, 3 (7), 996-1008.
39. Madan, B.; Chaudhary, G.; Cramer, S. M.; Chen, W., ELP-z and ELP-zz capturing scaffolds for the purification of immunoglobulins by affinity precipitation. J Biotechnol 2013, 163 (1), 10-6.
40. Sheth, R. D.; Bhut, B. V.; Jin, M.; Li, Z.; Chen, W.; Cramer, S. M., Development of an ELP—Z based mAb affinity precipitation process using scaled-down filtration techniques. J Biotechnol 2014, 192 Pt A, 11-9.
41. Kawashima, R.; Abei, M.; Fukuda, K.; Nakamura, K.; Murata, T.; Wakayama, M.; Seo, E.; Hasegawa, N.; Mizuguchi, H.; Obata, Y.; Hyodo, I.; Hamada, H.; Yokoyama, K. K., EpCAM- and EGFR-targeted selective gene therapy for biliary cancers using Z33-fiber-modified adenovirus. Int J Cancer 2011, 129 (5), 1244-53.
42. Kickhoefer, V. A.; Han, M.; Raval-Fernandes, S.; Poderycki, M. J.; Moniz, R. J.; Vaccari, D.; Silvestry, M.; Stewart, P. L.; Kelly, K. A.; Rome, L. H., Targeting vault nanoparticles to specific cell surface receptors. Acs Nano 2008, 3 (1), 27-36.
43. Freire, E.; Kawasaki, Y.; Velazquez-Campoy, A.; Schön, A., Characterisation of ligand binding by calorimetry. In Biophysical Approaches Determining Ligand Binding to Biomolecular Targets, 2011; pp 275-299.
44. Wiseman, T.; Williston, S.; Brandts, J. F.; Lin, L.-N., Rapid measurement of binding constants and heats of binding using a new titration calorimeter. Analytical biochemistry 1989, 179 (1), 131-137.
45. Demers, J.-P.; Mittermaier, A., Binding mechanism of an SH3 domain studied by NMR and ITC. Journal of the American Chemical Society 2009, 131 (12), 4355-4367.
46. van Eldijk, M. B.; Smits, F. C.; Thies, J. C.; Mecinovic, J.; van Hest, J. C., Thermodynamic investigation of Z33-antibody interaction leads to selective purification of human antibodies. J Biotechnol 2014, 179, 32-41.
47. Lund, L. N.; Christensen, T.; Toone, E.; Houen, G.; Staby, A.; St Hilaire, P. M., Exploring variation in binding of Protein A and Protein G to immunoglobulin type G by isothermal titration calorimetry. J Mol Recognit 2011, 24 (6), 945-52.

The invention claimed is:

1. An IgG binding immuno-amphiphile consisting of the amino acid sequence of SEQ ID NO: 1 conjugated at the N-terminus to a lauric acid moiety.

2. The IgG binding immuno-amphiphile of claim 1, wherein a peptide portion of the IgG binding immuno-amphiphile has an α-helical conformation when in an aqueous solution at a pH between 2.8 to 7.4.

3. A conjugate of the IgG binding immuno-amphiphile of claim 1 with Rhodamine B.

4. A method for purification of an antibody or an Fc fusion protein, comprising the steps of:

dissolving the IgG binding immuno-amphiphile of claim 1 in an aqueous solution at physiological pH, and aging overnight to make it self-assemble into immunofibers (IFs);

mixing a sample containing an antibody or an Fc fusion protein with the IFs, and allowing the IFs to bind the Fc portion of the antibody or Fc fusion protein and form an immunofiber-antibody complex or immunofiber-Fc fusion protein complex in solution;

separating the immunofiber-antibody complex or the immunofiber-Fc fusion protein complex from the solution; and dissociating the IFs from the antibody or Fc fusion protein and collecting the unbound antibody or Fc fusion protein.

5. The method of claim 4, wherein the IFs are separated from the antibody or Fc fusion protein by lowering the pH to elution condition and filtration or microfiltration.

6. The method of claim 4, wherein the IFs are separated from the antibody or Fc fusion protein by salt-induced precipitation and centrifugation.

7. The method of claim 4, wherein the IFs are separated from the antibody or Fc fusion protein by diafiltration.

8. The method of claim 4, wherein a peptide portion of the IgG binding immuno-amphiphile has an α-helical conformation when in an aqueous solution at a pH between 2.8 to 7.4.

9. The method of claim 4, wherein the IgG binding immuno-amphiphile is conjugated to Rhodamine B.

* * * * *

SEQUENCE LISTING

```
<160> NUMBER OF SEQ ID NOS: 3

<210> SEQ ID NO 1
<211> LENGTH: 33
<212> TYPE: PRT
<213> ORGANISM: artificial sequence
<220> FEATURE:
<223> OTHER INFORMATION: synthetic sequence

<400> SEQUENCE: 1

Phe Asn Met Gln Gln Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp

<210> SEQ ID NO 2
<211> LENGTH: 5
<212> TYPE: PRT
<213> ORGANISM: Artificial Sequence
<220> FEATURE:
<223> OTHER INFORMATION: synthetic sequence

<400> SEQUENCE: 2

Ile Lys Val Ala Val
1               5

<210> SEQ ID NO 3
<211> LENGTH: 4
<212> TYPE: PRT
<213> ORGANISM: Artificial Sequence
<220> FEATURE:
<223> OTHER INFORMATION: synthetic sequence

<400> SEQUENCE: 3

Arg Gly Asp Ser
1
```